(12) United States Patent
Kuo

(10) Patent No.: US 12,303,614 B2
(45) Date of Patent: *May 20, 2025

(54) COMPOSITIONS AND METHODS FOR IMPROVING MECHANICAL PROPERTIES OF A TISSUE OR FOR REGENERATING AN INJURED OR DISEASED TISSUE

(71) Applicant: University of Rochester, Rochester, NY (US)

(72) Inventor: Catherine K. Kuo, College Park, MD (US)

(73) Assignee: University of Rochester, Rochester, NY (US)

( * ) Notice: Subject to any disclaimer, the term of this patent is extended or adjusted under 35 U.S.C. 154(b) by 13 days.

This patent is subject to a terminal disclaimer.

(21) Appl. No.: 18/311,592

(22) Filed: May 3, 2023

(65) Prior Publication Data

US 2024/0009350 A1 Jan. 11, 2024

Related U.S. Application Data

(62) Division of application No. 16/800,151, filed on Feb. 25, 2020, now Pat. No. 11,679,178.

(60) Provisional application No. 62/810,021, filed on Feb. 25, 2019.

(51) Int. Cl.
*A61L 27/24* (2006.01)
*A61B 5/00* (2006.01)
*A61L 27/38* (2006.01)
*A61L 27/54* (2006.01)

(52) U.S. Cl.
CPC ............ *A61L 27/24* (2013.01); *A61B 5/0048* (2013.01); *A61L 27/3834* (2013.01); *A61L 27/54* (2013.01); *A61L 2300/254* (2013.01); *A61L 2300/414* (2013.01); *A61L 2430/06* (2013.01); *A61L 2430/10* (2013.01); *A61L 2430/20* (2013.01)

(58) Field of Classification Search
None
See application file for complete search history.

(56) References Cited

U.S. PATENT DOCUMENTS

| 11,679,178 | B2* | 6/2023 | Kuo | ...................... | A61B 5/0053 |
|---|---|---|---|---|---|
| | | | | | 424/423 |
| 2001/0016772 | A1 | 8/2001 | Lee et al. | | |
| 2004/0067833 | A1 | 4/2004 | Talish et al. | | |
| 2005/0025838 | A1 | 2/2005 | Badylak | | |
| 2006/0029588 | A1 | 2/2006 | Li et al. | | |
| 2006/0293724 | A1 | 12/2006 | Kronberg et al. | | |
| 2008/0274545 | A1 | 11/2008 | Kuo et al. | | |
| 2010/0047309 | A1 | 2/2010 | Lu et al. | | |
| 2011/0293685 | A1 | 12/2011 | Kuo et al. | | |
| 2017/0312392 | A1 | 11/2017 | Guilak et al. | | |
| 2018/0155447 | A1 | 6/2018 | Fan et al. | | |

FOREIGN PATENT DOCUMENTS

| WO | 14065863 A1 | 5/2014 |
|---|---|---|
| WO | 2017087754 A2 | 5/2017 |

OTHER PUBLICATIONS

Brown et al., "Comparative analysis of mesenchymal stem cell and embryonic tendon progenitor cell response to embryonic tendon biochemical and mechanical factors," Stem Cell Research & Therapy (2015); 6:89—8 pages.
Marturano et al., "Embryonically inspired scaffolds regulate tenogenically differentiating cells," Journal of Biomechanics (2016); 49:3281-3288.
Marturano et al., "Lysyl oxidase-mediated collagen crosslinks may be assessed as markers of functional properties of tendon tissue formation," Acta Biomaterialia (2014); 10:1370-1379.
Marturano et al., "Characterization of mechanical and biochemical properties of developing embryonic tendon," PNAS (2013); 110(16):6370-6375.
Kuo et al., "Mechanoactive Tenogenic Differentiation of Human Mesenchymal Stem Cells," Tissue Engineering: Part A (2008); 14:1615-1627.
Ng et al., "Establishing the Basis for Mechanobiology-Based Physical Tehrapy Protocols to Potentiate Cellular Healing and Tissue Regeneration," Frontiers in Biology (2017); 8:Article 303—13 pages.
Bhuvanasundar et al., "A molecular model of human Lysyl Oxidase (LOX) with optimal copper orientation in the catalytic cavity for induced fit docking studies with potential modulators," Biomedical Informatics (2014); 10(7):406-412.
Csiszar, Katalin, "Lysyl Oxidases: A Novel Multifunctional Amine Oxidase Family," Progress in Nucleic Acid Research and Molecular Biology (copyright 2001); 70:1-32.
Cai et al., "The Role of the Lysyl Oxidases in Tissue Repair and Remodeling: A Consise Review," Tissue Eng Regen Med (2017); 14(1):15-30.
Chica et al., "Semi-rational approaches to engineering enzyme activity: combining the benefits of directed evolution and rational design," Current Opinion in Biotechnology (2005); 16:378-384.
Singh et al., "Protein Engineering Approaches in the Post-Genomic Era," Current Protein and Peptide Science (2017); 18:1-11.

\* cited by examiner

*Primary Examiner* — Christian L Fronda
(74) *Attorney, Agent, or Firm* — Fox Rothschild LLP

(57) ABSTRACT

The present invention relates to enhancing mechanical properties of tissue such as collagenous or collagen-containing or elastin-containing tissue (e.g., tendons, ligaments, and cartilage) and treating related musculoskeletal and non-musculoskeletal conditions or injuries.

18 Claims, 5 Drawing Sheets
Specification includes a Sequence Listing.

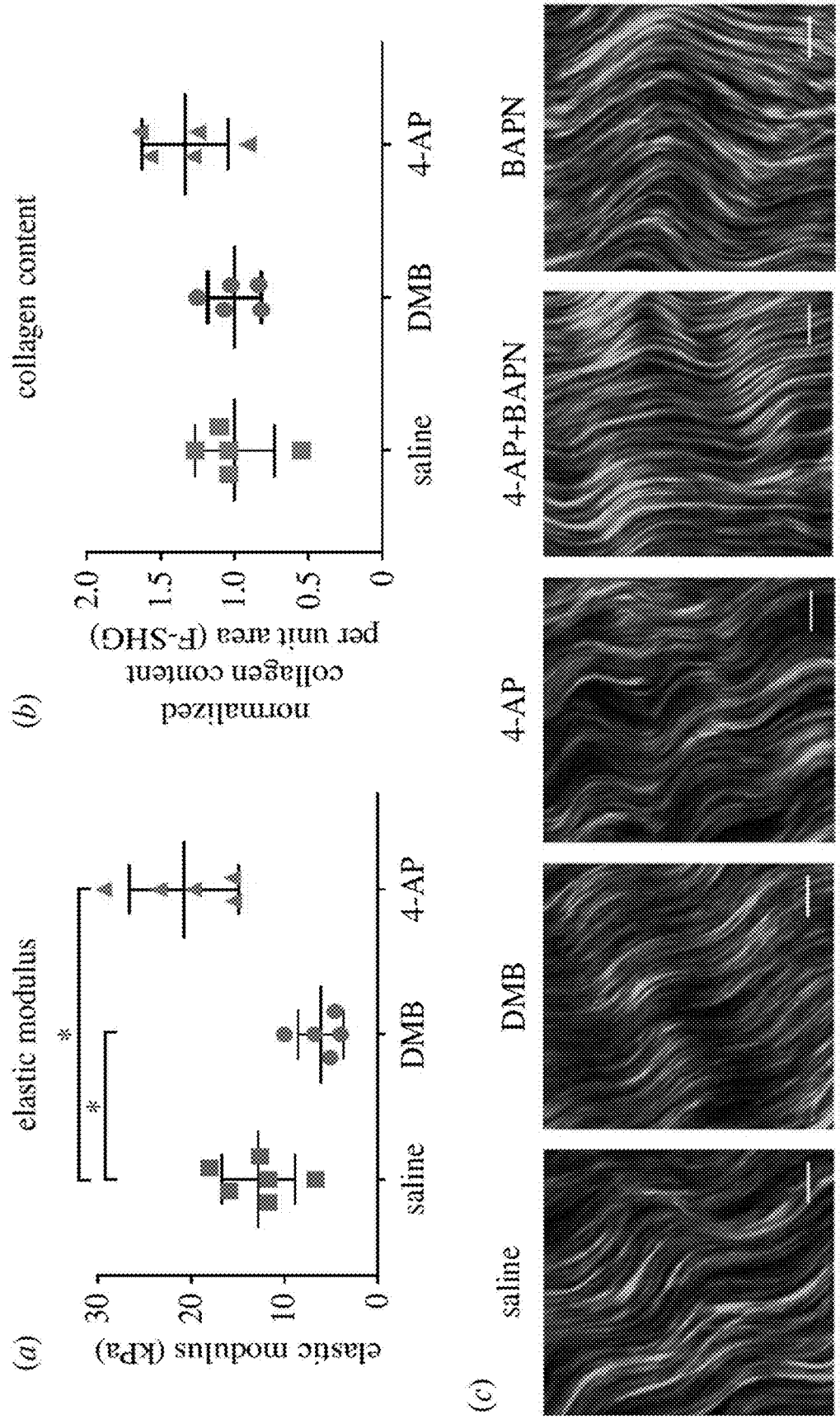
FIGS. 1A, 1B, and 1C

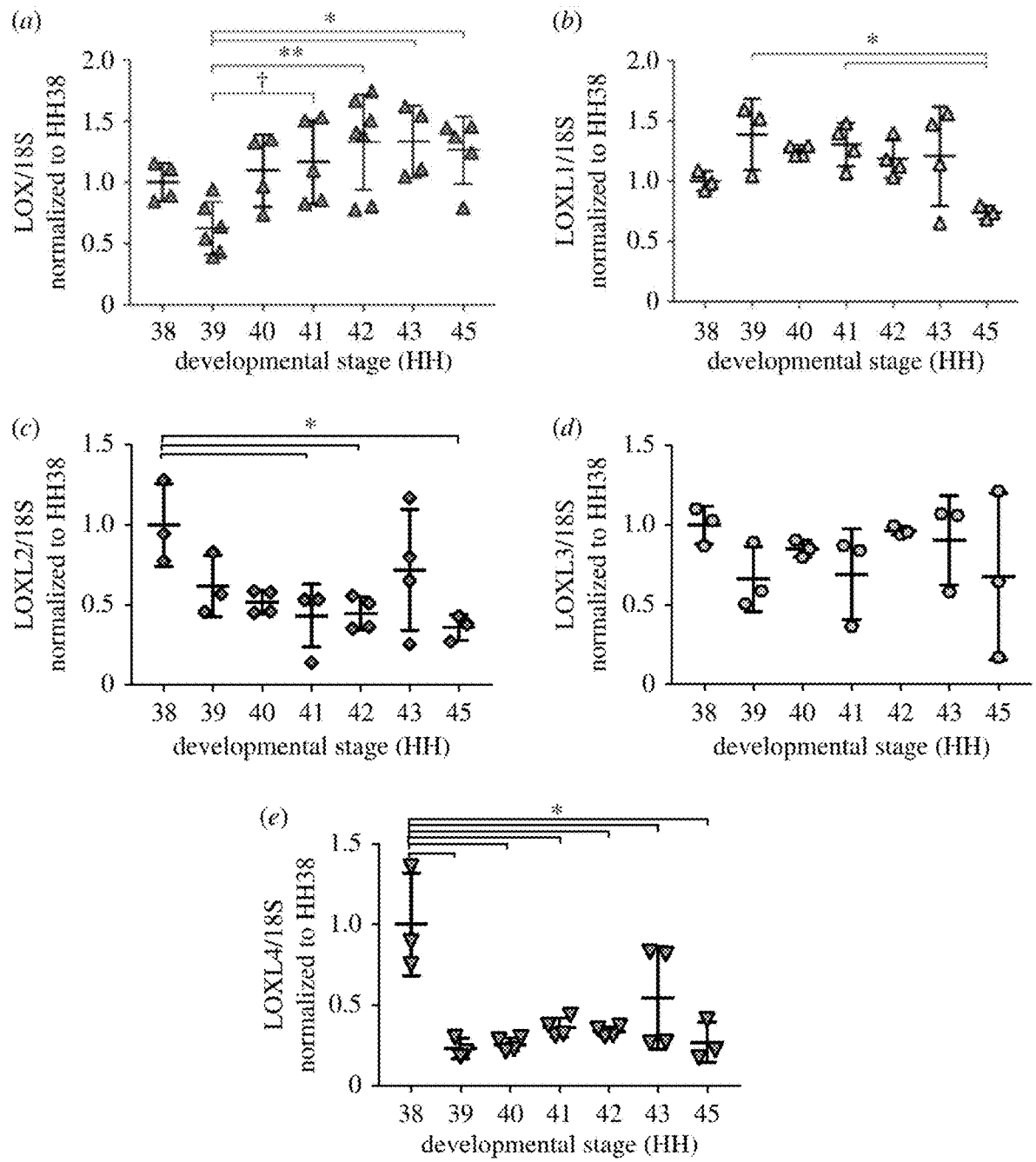
FIGS. 2A, 2B, 2C, 2D, and 2E

FIGS. 6A, 6B, 6C, 6D, 6E, and 6F

```
                            SEQUENCE LISTING

Sequence total quantity: 17
SEQ ID NO: 1            moltype = AA  length = 417
FEATURE                 Location/Qualifiers
source                  1..417
                        mol_type = protein
                        organism = Homo sapiens
SEQUENCE: 1
MRFAWTVLLL GPLQLCALVH CAPPAAGQQQ PPREPPAAPG AWRQQIQWEN NGQVFSLLSL   60
GSQYQPQRRR DPGAAVPGAA NASAQQPRTP ILLIRDNRTA AARTRTAGSS GVTAGRPRPT  120
ARHWFQAGYS TSRARERGAS RAENQTAPGE VPALSNLRPP SRVDGMVGDD PYNPYKYSDD  180
NPYYNYYDTY ERPRPGGRYR PGYGTGYFQY GLPDLVADPY YIQASTYVQK MSMYNLRCAA  240
EENCLASTAY RADVRDYDHR VLLRFPQRVK NQGTSDFLPS RPRYSWEWHS CHQHYHSMDE  300
FSHYDLLDAN TQRRVAEGHK ASFCLEDTSC DYGYHRRFAC TAHTQGLSPG CYDTYGADID  360
CQWIDITDVK PGNYILKVSV NPSYLVPESD YTNNVVRCDI RYTGHHAYAS GCTISPY     417

SEQ ID NO: 2            moltype = AA  length = 21
FEATURE                 Location/Qualifiers
source                  1..21
                        mol_type = protein
                        organism = Homo sapiens
SEQUENCE: 2
MRFAWTVLLL GPLQLCALVH C                                             21

SEQ ID NO: 3            moltype = AA  length = 249
FEATURE                 Location/Qualifiers
source                  1..249
                        mol_type = protein
                        organism = Homo sapiens
SEQUENCE: 3
DDPYNPYKYS DDNPYYNYYD TYERPRPGGR YRPGYGTGYF QYGLPDLVAD PYYIQASTYV   60
QKMSMYNLRC AAEENCLAST AYRADVRDYD HRVLLRFPQR VKNQGTSDFL PSRPRYSWEW  120
HSCHQHYHSM DEFSHYDLLD ANTQRRVAEG HKASFCLEDT SCDYGYHRRF ACTAHTQGLS  180
PGCYDTYGAD IDCQWIDITD VKPGNYILKV SVNPSYLVPE SDYTNNVVRC DIRYTGHHAY  240
ASGCTISPY                                                          249

SEQ ID NO: 4            moltype = AA  length = 135
FEATURE                 Location/Qualifiers
source                  1..135
                        mol_type = protein
                        organism = Homo sapiens
SEQUENCE: 4
RYSWEWHSCH QHYHSMDEFS HYDLLDANTQ RRVAEGHKAS FCLEDTSCDY GYHRRFACTA   60
HTQGLSPGCY DTYGADIDCQ WIDITDVKPG NYILKVSVNP SYLVPESDYT NNVVRCDIRY  120
TGHHAYASGC TISPY                                                   135

SEQ ID NO: 5            moltype = AA  length = 574
FEATURE                 Location/Qualifiers
source                  1..574
                        mol_type = protein
                        organism = Homo sapiens
SEQUENCE: 5
MALARGSRQL GALVWGACLC VLVHGQQAQP GQGSDPARWR QLIQWENNGQ VYSLLNSGSE   60
YVPAGPQRSE SSSRVLLAGA PQAQQRRSHG SPRRQAPSL  PLPGRVGSDT VRGQARHPFG  120
FGQVPDNWRE VAVGDSTGMA RARTSVSQQR HGGSASSVSA SAFASTYRQQ PSYPQQFPYP  180
QAPFVSQYEN YDPASRTYDQ GFVYYRPAGG GVGAGAAYA  SAGVIYPYQP RARYEEYGGG  240
EELPEYPPQG FYPAPERPYV PPPPPPPDGL DRRYSHSLYS EGTPGFEQAY PDPGPEAAQA  300
HGGDPRLGWY PPYANPPPEA YGPPRALEPP YLPVRSSDTP PPGGERNGAQ QGRLSVGSVY  360
RPNQNGRGLP DLVPDPNYVQ ASTYVQRAHL YSLRCAAEEK CLASTAYAPE ATDYDVRVLL  420
RFPQRVKNQG TADFLPNRPR HTWEWHSCHQ HYHSMDEFSH YDLLDAATGK KVAEGHKASF  480
CLEDSTCDFG NLKRYACTSH TQGLSPGCYD TYNADIDCQW IDITDVQPGN YILKVHVNPK  540
YIVLESDFTN NVVRCNIHYT GRYVSATNCK IVQS                              574

SEQ ID NO: 6            moltype = DNA length = 20
FEATURE                 Location/Qualifiers
misc_feature            1..20
```

```
                    note = Synthesized primer
source              1..20
                    mol_type = other DNA
                    organism = synthetic construct
SEQUENCE: 6
tcgggcggat gttagagact                                                   20

SEQ ID NO: 7        moltype = DNA  length = 20
FEATURE             Location/Qualifiers
misc_feature        1..20
                    note = Synthesized primer
source              1..20
                    mol_type = other DNA
                    organism = synthetic construct
SEQUENCE: 7
agctggcgtc taacaagtca                                                   20

SEQ ID NO: 8        moltype = DNA  length = 20
FEATURE             Location/Qualifiers
misc_feature        1..20
                    note = Synthesized primer
source              1..20
                    mol_type = other DNA
                    organism = synthetic construct
SEQUENCE: 8
tgctacgaca cctacaacgc                                                   20

SEQ ID NO: 9        moltype = DNA  length = 20
FEATURE             Location/Qualifiers
misc_feature        1..20
                    note = Synthesized primer
source              1..20
                    mol_type = other DNA
                    organism = synthetic construct
SEQUENCE: 9
gtggttttgg gctcatggtg                                                   20

SEQ ID NO: 10       moltype = DNA  length = 21
FEATURE             Location/Qualifiers
misc_feature        1..21
                    note = Synthesized primer
source              1..21
                    mol_type = other DNA
                    organism = synthetic construct
SEQUENCE: 10
caattccttg catccccaac c                                                 21

SEQ ID NO: 11       moltype = DNA  length = 20
FEATURE             Location/Qualifiers
misc_feature        1..20
                    note = Synthesized primer
source              1..20
                    mol_type = other DNA
                    organism = synthetic construct
SEQUENCE: 11
tagggccagg aatgctcaga                                                   20

SEQ ID NO: 12       moltype = DNA  length = 19
FEATURE             Location/Qualifiers
misc_feature        1..19
                    note = Synthesized primer
source              1..19
                    mol_type = other DNA
                    organism = synthetic construct
SEQUENCE: 12
agttggcaca ctcgtaccg                                                    19

SEQ ID NO: 13       moltype = DNA  length = 23
FEATURE             Location/Qualifiers
misc_feature        1..23
                    note = Synthesized primer
source              1..23
                    mol_type = other DNA
                    organism = synthetic construct
SEQUENCE: 13
catcttcaca ccaacgacat cct                                               23

SEQ ID NO: 14       moltype = DNA  length = 20
FEATURE             Location/Qualifiers
```

```
                              -continued misc_feature         1..20
                     note = Synthesized primer
source               1..20
                     mol_type = other DNA
                     organism = synthetic construct
SEQUENCE: 14
tgcgatgatg gcttcgactt                                        20

SEQ ID NO: 15        moltype = DNA  length = 20
FEATURE              Location/Qualifiers
misc_feature         1..20
                     note = Synthesized primer
source               1..20
                     mol_type = other DNA
                     organism = synthetic construct
SEQUENCE: 15
ctggccgtaa gtagcactgt                                        20

SEQ ID NO: 16        moltype = DNA  length = 21
FEATURE              Location/Qualifiers
misc_feature         1..21
                     note = Synthesized primer
source               1..21
                     mol_type = other DNA
                     organism = synthetic construct
SEQUENCE: 16
aacgggccca tgattaagag g                                      21

SEQ ID NO: 17        moltype = DNA  length = 20
FEATURE              Location/Qualifiers
misc_feature         1..20
                     note = Synthesized primer
source               1..20
                     mol_type = other DNA
                     organism = synthetic construct
SEQUENCE: 17
ttgcgccggt ccaagaattt                                        20
```

COMPOSITIONS AND METHODS FOR IMPROVING MECHANICAL PROPERTIES OF A TISSUE OR FOR REGENERATING AN INJURED OR DISEASED TISSUE

CROSS REFERENCE TO RELATED APPLICATIONS

This application is a divisional of U.S. patent application Ser. No. 16/800,151 filed on Feb. 25, 2020, which claims priority to U.S. Provisional Application No. 62/810,021 filed on Feb. 25, 2019. The content of the applications are incorporated herein by reference in their entirety.

GOVERNMENT INTERESTS

This invention was made with government support under AR072886 awarded by National Institutes of Health and CMMI-1560965 awarded by National Science Foundation. The government has certain rights in the invention.

SEQUENCE LISTING

This application contains a Sequence Listing which has been submitted electronically in XMIL format and is hereby incorporated by reference in its entirety. Said XML copy, created on May 3, 2023, is named 16111801102.xml and is 21,891 bytes in size.

FIELD OF THE INVENTION

This invention relates to a tissue engineering and regenerative medicine. Specifically, the present disclosure involves enhancing mechanical properties of tissue containing collagen or elastin such as tendons, ligaments, cartilage, heart, lung, and skin and treating related musculoskeletal or non-musculoskeletal conditions or injuries.

BACKGROUND OF THE INVENTION

Musculoskeletal conditions or injuries represent a critical health concern. According to the American Academy of Orthopedic Surgeons, over one in four Americans have a musculoskeletal impairment, costing the United States close to $850 billion each year. It was estimated that annually musculoskeletal-related conditions in the US account for 132 million doctor visits, 29 million emergency department visits, and 15 million hospital stays. There is a need for enhancing mechanical properties of tissue and thereby treating related musculoskeletal conditions or injuries.

SUMMARY OF INVENTION

This invention relates to enhancing mechanical properties of tissue via increasing lysyl oxidase activity or mechanical stimulation and treating related musculoskeletal or non-musculoskeletal tissues (e.g., skin) conditions or injuries.

In one aspect, the invention features a method for (i) improving a mechanical property of a tissue or a component thereof or (ii) regenerating an injured or diseased tissue or developing embryonic/fetal tissue or a component thereof or (iii) enhance mechanical properties of a healthy tissue in a subject. The method comprises applying a mechanical stimulation to the tissue or cells therein. In some embodiments, the method further comprises increasing a level of lysyl oxidase (LOX) activity in the tissue.

In another aspect, the invention provides a method for (i) improving a mechanical property of a tissue or a component thereof or (ii) regenerating an injured tissue or a component thereof in a subject. The method comprises increasing a level of LOX activity in the tissue. In some embodiments, the method further comprises applying a mechanical stimulation to the tissue or cells therein.

In the above-described methods, examples of the mechanical stimulation include a dynamic stimulation, a cyclic stimulation, a static stimulation, a deformation, a tensile stimulation, a compressive stimulation, a torsion stimulation, a shear stimulation, substrate stiffness, and a mechanical loading. The mechanical stimulation can be independent, or the mechanical stimulation can be combined with other types of treatments as described herein. One or more of the mechanical stimuli can also be combined. The mechanical loading can comprise a static loading, a dynamic loading, a cyclic loading, a compression, shear, torsion, or deformation.

The tissue mentioned above can be any tissue of interest. Examples of the tissue include, but not limited to, a healthy or normal tissue, an injured tissue, a diseased tissue, an aging tissue, an adult tissue, or a developing embryonic/fetal tissue. The tissue or tissues can comprise a natural tissue, an engineered tissue, an embryonic tissue, a postnatal tissue, a tissue in vitro, or a tissue in vivo. The mechanical property of the tissue can be one selected from the group consisting of elastic modulus, tensile strength, torsional strength, elongation to break, hardness, compressive strength, burst strength, toughness, impact strength, torsion, failure load, and stiffness.

In the above-described methods, the LOX activity can be an activity of LOX or a LOX like (LOXL) protein, (e.g., LOX-like 1, LOX-like 2, LOX-like 3, or LOX-like 4). Increasing a level of LOX activity can be carried out by delivering to the tissue a LOX/LOXL enhancer. Examples of the enhancer include an agent selected from the group consisting of a LOX or LOXL (LOX/LOXL) polypeptide, a pre-pro LOX/LOXL polypeptide, a pro LOX/LOXL polypeptide, a nucleic acid encoding one or more of said polypeptides, a viral particle having said nucleic acid, an engineered cell expressing having said nucleic acid, bone morphogenetic protein-1 (BMP-1), Fibronectin, Tolloid, Copper, Vitamin B6, Ascorbic acid, and Procollagen c proteinase.

In some embodiments, the methods described above can further comprise administering a population of cells to the tissue. The cells can be (i) collagen-producing or elastin-producing cells or progenitor cells thereof or (ii) engineered to release a specific factor that directly or indirectly promotes LOX/LOXL or pro-LOX/pro-LOXL gene expression, LOX/LOXL or pro-LOX/pro-LOXL protein expression, or LOX/LOXL enzyme activity.

The invention further provides a pharmaceutical composition comprising (i) a LOX/LOXL enhancer, and (ii) a pharmaceutically acceptable carrier or excipient. Also provided is a kit comprising one or more of the LOX/LOXL enhancers and a packaging material.

The details of one or more embodiments of the invention are set forth in the description below. Other features, objectives, and advantages of the invention will be apparent from the description and from the claims.

BRIEF DESCRIPTION OF THE DRAWINGS

FIGS. 1A, 1B, and 1C are a set of diagrams and photographs showing effects of paralysis (decamethonium bromide (DMB) treatment) and hypermotility (4-aminopyridine (4-AP) treatment) on Hamburger-Hamilton stage (HH)43 calcaneal tendons after 48 h (N≥5). (a) DMB treatment led to lower elastic modulus than saline treatment. 4-AP treatment led to higher elastic modulus than saline treatment. (b) Normalized fibrillar collagen content did not change with DMB treatment or 4-AP treatment compared to saline controls. (c) Representative images of fibrillar collagen detected by forward second harmonic generation (F-SHG) for saline, DMB, 4-AP, 4-AP+β-aminopropionitrile (BAPN), and BAPN treatments. (Scale bar: 10 mm; *p<, 0.05).

FIGS. 2A, 2B, 2C, 2D, and 2E are a set of diagrams showing LOX and LOXL1-4 exhibited distinct gene expression profiles in developing calcaneal tendons (N≥3). (a) LOX mRNA expression levels of HH41 to hHH45 tendons were higher than that of HH39. (b) LOXL1 mRNA maintained relatively constant levels until decreasing at HH45. (c) LOXL2 levels decreased from HH38 to HH45. (d) LOXL3 levels did not change from HH38 to HH45. (e) LOXL4 mRNA levels decreased from HH38 to HH39 and then remained constant to HH45. (*p<0.05; **p<0.01; †0.05<p<0.08).

DETAILED DESCRIPTION OF THE INVENTION

Figures 3A, 3B:
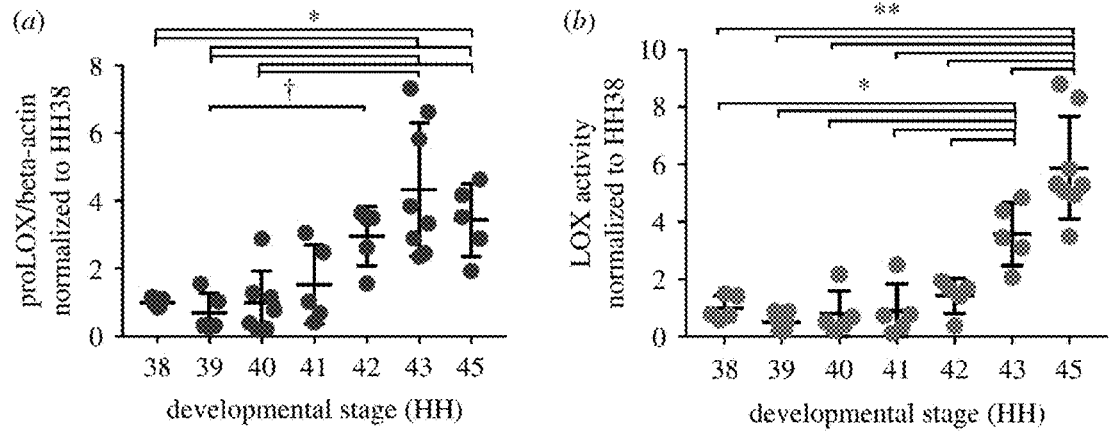
FIGS. 3A and 3B are a set of diagrams showing that ProLOX and LOX activity levels increased in calcaneal tendons during development (N≥5). (a) ProLOX levels increased from HH38 to HH42 and then plateaued. (b) LOX activity levels were constant from HH38 to HH42 and then increased from HH42 to HH45. (*p<0.05; **p<0.01; †0.05<p<0.08).

This invention relates to tissue engineering, regenerative medicine, physical rehabilitation, or enhancement of various tissues. It involves enhancing mechanical properties of tissue (such as tendons, ligaments, and cartilage), improving tissue mechanical properties, and treating related musculoskeletal conditions or injuries. As disclosed herein, the tissue engineering can include artificially imposing mechanical stimulation to engineered tissues or to explant tissues—which can then be implanted. Regenerative medicine via physical rehabilitation can utilize physical therapy in the form of passive movement or muscle-generated forces to mechanically stimulate tissue(s) to treat conditions or injuries. In some embodiments, massage could be used to mechanically stimulate tissues (deep tissues, e.g., muscle; or skin; etc.).

Tissue Mechanical Property and Mechanical Loading

Certain aspects of this invention are based, at least in part, on an unexpected discovery that embryo movements regulate mechanical property development of tissues, such as tendon.

Tendons transmit forces from muscles to bones to enable skeletal motility. During development, tendons begin to bear load at the onset of embryo movements. Using the chick embryo model, study disclosed herein showed that altered embryo movement frequency led to changes in elastic modulus of calcaneal tendon. In particular, paralysis led to decreased modulus, whereas hypermotility led to increased modulus. Paralysis also led to reductions in activity levels of LOX, an enzyme for crosslinking-mediated elaboration of tendon mechanical properties. Additionally, inhibition of LOX activity abrogated hypermotility-induced increases in modulus. Taken together, the findings disclosed herein suggest embryo movements are critical for tendon mechanical property development and implicate LOX in this process. These findings expand current knowledge of how functional tendons form during development and could guide future clinical approaches to treat tendon defects associated with abnormal mechanical loading in utero.

Tendons are load-bearing collagenous tissues that enable skeletal motility. Kicking depends heavily on calcaneal tendons to transmit forces from the calf muscle to the calcaneal bone. Embryo movements, such as kicking, have been implicated as critical regulators of musculoskeletal tissue development (1-8). Deprivation of movement via treatment with DMB results in abnormal development of bone, meniscus, and joint (1, 3, 4). In contrast, 4-AP treatment to increase chick embryo motility increased bone growth (5, 9). Fewer studies have focused on mechanical regulation of tendon development. Specifically, paralysis of early stage (e.g., HH24 and HH28) chick embryos with DMB leads to abnormal tendon marker expression patterns and tendon tissue morphology compared to controls (3, 6). While these studies implicate movement as a regulator of tendon development, the influence of mechanical loading on the formation of a mechanically functional tendon had not been investigated.

With atomic force microscopy (AFM), non-linear increases in embryonic calcaneal tendon modulus from HH28 to HH43 (~day 5.5 to 17) were characterized. Interestingly, the most dramatic increases in tendon modulus occur during stages that coincide with heightened movement activity (frequency). In particular, kicking frequencies peak at HH40 and HH43, the same stages when chick embryo calcaneal tendon modulus increases dramatically. For reference, the chick embryo is near full term by HH45 (hatches at day 21), when the tendon is nearly ready to function as a load-bearing tissue during postnatal activities (walking, jumping, etc.). In the examples described below, study was carried out to examine how embryo movement frequency influences mechanical property development during these critical stages of functional tendon formation.

The findings disclosed herein provide evidence that mechanical cues are critical for embryonic tendon development. In particular, frequency of movements, such as kicking, can significantly influence tendon mechanical property elaboration and skeletal development. Additionally, the findings indicate LOX as a key player in this process. This information impacts clinical approaches to treat musculoskeletal abnormalities that result from aberrant embryonic or fetal movements in utero. In addition, mechanics in tendon development can be used to inform tissue engineering (e.g., tendon) and regeneration strategies.

Improving Mechanical Property

In some embodiments, the present disclosure provides methods for improving mechanical property of a tissue (e.g., tendon, ligament, and cartilage). As disclosed herein, the methods can lead to an increase in collagen crosslinking, which leads to an increase in mechanical property (e.g., modulus). Accordingly, collagenous tissue produced using methods of the present disclosure is extensively cross-linked and has enhanced mechanical properties, such as high(er) elastic modulus and others disclosed herein. Specifically, the present disclosure involves an enzyme-mediated collagen-crosslinking process to produce tissue such as tendon, ligament, or cartilage, and to enhance its mechanical properties, maturation, and integration.

In some embodiments, this invention provides methods for improving engineered tissues. An example of a tissue suitable for the methods of the present disclosure is an elastin-containing tissue or a collagen-containing, or collagenous, tissue, such as tendon, ligament, and cartilage. Collagenous tissue contains an intricate architecture of collagen crosslinks, as well as a variety of other components. As this collagen network structure and associated properties is inherent to native collagenous tissues, the tissue engineering disclosed herein can be used to produce tissues that mimic or are superior to native tissues.

Accordingly, this invention relates to methods of producing collagenous tissue possessing a high tensile strength involving treating connective tissue cells under conditions effective for formation of enzyme-mediated collagen cross-links to produce collagenous tissue possessing a high tensile strength. Conditions effective for formation of enzyme-mediated collagen cross-links to produce a collagenous tissue having a high tensile strength may comprise application of applying a mechanical stimulation and/or a LOX enhancer.

Mechanical Load

Cells, such as chondrocytes in cartilage, fibrochondrocytes in menisci, or tenocytes and fibroblasts in tendon and ligament, are able to alter their metabolic activity in response to applied mechanical loads. Both the level of strain applied and the dynamic frequency are important in determining this response. These processes are believed to be major factors in determining cellular activity in these tissues. The mechanisms by which cells detect and respond to mechanical load are termed mechanotransduction pathways and are complex and poorly understood. Mechanotransduction events may be resolved into extracellular components including cell deformation, hydrostatic pressures and streaming potentials, followed by intracellular signaling events such as intracellular calcium fluxes, cAMP production and cytoskeletal alterations which finally lead to altered effector cell response.

The findings disclosed herein provide evidence that mechanical cues are critical for embryonic tendon development and that LOX is a key player in this process. The mechanics in tendon development can be used for tissue engineering and regeneration.

Some embodiments of the present invention may induce alterations in cell behavior in response to mechanical loading through many of the aforementioned mechanotransduction pathways. Mechanical stimulation or loading may be applied to cells in situ within a target tissue. Alternatively, a mechanical stimulation or loading may be applied to a cell-containing implant/construct prior to implantation to the target tissue using specially designed mechanical stimulation or applied to the cells within the construct post implantation through defined exercise regimes or through externally applied regimes such as continuous passive motion regimes. Mechanical stimulation or loading regimes, applied in a static or dynamic manner may take a variety of forms including, e.g., uniaxial compression or tension or hydrostatic pressure. Static and dynamic peak strain amplitude may be in the range between 0.5-30% (e.g., 1-25%, 5-20%, whilst dynamic frequencies should range from 0-10 Hz (e.g., 0.01-5 Hz, 0.1-3 Hz).

In some embodiments, exposure to a mechanical stimulation or loading can be achieved by consistently applying strain (i.e., applying a force that causes a change in length) or by applying stress (i.e., applying a mechanical load) to the tissue or implant over a predetermined period of time. Alternatively, mechanical stimulation or loading can be achieved by applying stress or strain to the tissue or implant in a cyclical pattern, for example, applying stress or strain for 1 minute every 5 minutes over a total time of 48 hours. The stress or strain can be constant throughout the time period, or alternatively, the stress or strain can vary. The amount of stress or strain can vary, for example, from 5% to 15% using an appropriate device, such as a load cell. The stress or strain can be applied in a uniaxial or multiaxial direction. The amount of strain applied can be measured in the cell culture systems by any means known in the art, for example, by laser measurements using laser beams and deflection times. Means for applying mechanical stimulation or loading are known in the art. Examples are described in US20180216057, US20010016772, US20050025838, and US20040067833, which are incorporated by reference in their entireties.

Mechanical stimulation or loading can be used together with a LOX. In some embodiments, a LOX can be in its active form, while in others LOX can be in an inactive form (e.g., a pro-enzyme or pre-pro-enzyme). Conditions effective for formation of enzyme-mediated collagen cross-links to produce a collagenous or elastogenic tissue having a high tensile strength may comprise exogenous application of one or more additional enhancers described herein and/or additional enzymes (such as glucose oxidase and catalase). Conditions effective for the formation of enzyme-mediated collagen cross-links to produce a collagenous tissue having a high tensile strength may comprise culturing connective tissue cells under hypoxic conditions. In some embodiments, the level of enzyme-mediated collagen-crosslinks is directly proportional to the concentration of exogenously—supplied or endogenously expressed LOX present during the treating step.

In some embodiments, a collagenous tissue treated with a method of this invention possesses a high tensile strength and can have an elastic modulus value higher (e.g., at least 1.5, 2, 3, 4, 5, 6, 7, 8, 9, 10-fold, or more) than the elastic modulus value of a control collagenous tissue.

The methods and compositions described herein may find use as in treating diseases and syndromes related to collagen or elastin crosslinking deficiency (e.g., osteolathyrism, Ehlers Danlos syndrome Type IV, etc.).

Lysyl Oxidase and Lysyl Oxidase-Like (LOXL) Proteins

Lysyl oxidase is an extracellular copper-dependent enzyme that catalyzes formation of aldehydes from lysine residues in collagen and elastin precursors. LOX catalyzes oxidative deamination of peptidyl lysine and hydroxylysine residues in collagens, and peptidyl lysine residues in elastin. The resulting peptidyl aldehydes spontaneously condense and undergo oxidation reactions to form the lysine-derived covalent cross-links required for the normal structural integrity of the extracellular matrix. In the reaction of lysyl oxidase with its substrates, hydrogen peroxide and ammonium are released in quantities stoichiometric with the peptidyl aldehyde product. See, e.g., Kagan et al., J. Cell. Biochem. 88:660-72 (2003).

Lysyl oxidase is secreted into the extracellular environment where it is then processed by proteolytic cleavage to a functional 30 (kilo daltons) kDa enzyme and an 18 kDa propeptide. The 30 kDa lysyl oxidase is enzymatically active whereas the 50 kDa proenzyme is not. Procollagen C-proteinases process pro-lysyl oxidase to its active form and are products of the Bmpl, TII1 and TII2 genes. The localization of the enzyme is mainly extracellular, although processed lysyl oxidase also localizes intracellularly and nuclearly. Sequence coding for the propeptide is moderately (60-70%) conserved among LOX and the LOXL proteins, whereas the sequence coding for the C-terminal 30 kDa region of the proenzyme in which the active site is located is highly conserved (approximately 95%). See Kagan et al., J. Cell Biochem. 59:329-38 (1995).

Five different lysyl oxidases are known to exist in both humans and mice, LOX and four LOX related, or LOX-like proteins (LOXL1, LOXL2, LOXL3, and LOXL4). LOX and the LOX-like proteins are referred to collectively as "LOX/LOXL" or "lysyl oxidase type enzymes" for the purposes of the present disclosure. The five forms of lysyl oxidases reside on five different chromosomes. These family members show some overlap in structure and function, but appear to have distinct functions as well. For example, although the main activity of LOX is the oxidation of specific lysine residues in collagen and elastin outside of the cell, it may also act intracellularly, where it may regulate gene expression. In addition, LOX induces chemotaxis of monocytes, fibroblasts and smooth muscle cells. Further, a deletion of LOX in knockout mice appears to be lethal at parturition (Hornstra et al., J. Biol. Chem. 278:14387-14393 (2003)), whereas LOXL deficiency causes no severe developmental phenotype (Bronson et al., Neurosci. Lett. 390:118-122 (2005)).

The main activity of LOX is the oxidation of specific lysine residues in collagen and elastin outside of the cell, however, it may also act intracellularly, where it may regulate gene expression (Li et al., Proc. Natl. Acad. Sci. USA 94:12817-12822 (1997), Giampuzzi et al., J. Biol. Chem. 275:36341-36349 (2000)). In addition, LOX induces chemotaxis of monocytes, fibroblasts and smooth muscle cells (Lazarus et al., Matrix Biol. 14:727-731 (1995), Nelson et al., Proc. Soc. Exp. Biol. Med. 188:346-352 (1988)). LOX itself is induced by a number of growth factors and steroids such as TGF-β, TNF-α and interferon (Csiszar, Prog. Nucl. Acid Res. 70:1-32 (2001)).

As used herein, the term "lysyl oxidase" refers to an enzyme that catalyzes the following reaction: peptidyl-L-lysyl-peptide+$O_2$+$H_2O$ ->peptidyl-allysyl-peptide+$NH_3$+$H_2OZ$. Other synonyms for lysyl oxidase (EC 1.4.3.13) include protein-lysine 6-oxidase and protein-L-lysine: oxygen 6-oxidoreductase (deaminating). See, e.g., Harris et al., Biochim. Biophys. Acta 341:332-44 (1974); Rayton et al., J. Biol. Chem. 254:621-26 (1979); Stassen, Biophys. Acta 438:49-60 (1976). A copper-containing quinoprotein with a lysyl adduct of tyrosyl quinone at its active center, LOX catalyzes the oxidation of peptidyl lysine to result in the formation of peptidyl alpha-aminoadipic-delta-semialdehyde. Once formed, this semialdehyde can spontaneously condense with neighboring aldehydes or with other lysyl groups to form intra- and interchain cross-links. See, e.g., Rucker et al., Am. J. Clin. Nutr. 67:996S-1002S (1998).

An example of lysyl oxidase or lysyl oxidase-like protein include the enzyme having an amino acid sequence substantially identical to a polypeptide expressed or translated from one of the following sequences: EMBL/GenBank accession numbers: M94054; AAA59525.1; 545875; AAB23549.1; 578694; AAB21243.1; AF03929 I; AAD02130.1; BC074820; AAH74820.1; BC074872; AAH74872.1; M84150; and AAA59541.1. Additional examples include those described in e.g., US20180155447, US20060029588, and WO2014065863.

LOX has highly conserved protein domains, conserved in several species including human, mouse, rat, chicken, fish and Drosophila. Shown below a 417 amino acid (aa) human lysyl oxidase (hLOX, AAA59525.1, SEQ ID NO: 1). The human LOX family has a highly conserved C-terminal region containing the 205 amino acid residues (SEQ ID NO: 3) and in particular the aa 283-aa 417 (SEQ ID NO: 4, in bold in the sequence shown below) LOX catalytic domain. See e.g., Bhuvanasundar et al. Bioinformation, 2014 Jul. 22; 10(7):406-12 and Csiszar, Prog Nucleic Acid Res Mol Biol. 2001; 70:1-32, both of which are incorporated herein by reference in their entireties. The conserved aa 283-aa 417 region contains the copper binding (Cu), conserved cytokine receptor like domain (CRL), and the lysyl-tyrosylquinone cofactor site (LTQ). The predicted extracellular signal sequences are known in the art (See e.g., U.S. 20180155447, which is incorporated herein by reference in its entirety). Twelve cysteine residues are also similarly conserved, wherein two of them reside within the prepropeptide region and ten are in the catalytically active processed form of LOX (Csiszar, Prog. Nucl. Acid Res. 70:1-32 (2001)). The conserved region also includes a fibronectin binding domain.

One embodiment of LOX is human lysyl oxidase (hLOX, AAA59525.1, 417 aa):

(SEQ ID NO: 1)
MRFAWTVLLLGPLQLCALVHCAPPAAGQQQPPREPPAAPGAWRQQIQWE

NNGQVFSLLSLGSQYQPQRRRDPGAAVPGAANASAQQPRTPILLIRDNR

TAAARTRTAGSSGVTAGRPRPTARHWFQAGYSTSRARERGASRAENQTA

PGEVPALSNLRPPSRVDGMVGDDPYNPYKYSDDNPYYNYYDTYERPRPG

GRYRPGYGTGYFQYGLPDLVADPYYIQASTYVQKMSMYNLRCAAEENCL

ASTAYRADVRDYDHRVLLRFPQRVKNQGTSDFLPSRPRYSWEWHSCHQH

YHSMDEFSHYDLLDANTQRRVAEGHKASFCLEDTSCDYGYHRRFACTAH

TQGLSPGCYDTYGADIDCQWIDITDVKPGNYILKVSVNPSYLVPESDYT

NNVVRCDIRYTGHHAYASGCTISPY

The prepropeptide region of this hLOX contains the signal peptide (underlined, SEQ ID NO: 2), and is cleaved, the cleavage site predicted to be between Cys21-Ala22 (bold above), to generate a signal sequence peptide and a 48 kDa amino acid propeptide form of LOX, which is still inactive. The propeptide is N-glycosylated during passage through the Golgi that is secreted into the extracellular environment where the proenzyme, or propeptide, is cleaved between Gly168-Asp169 (bold above) by a metalloendoprotease, a procollagen C-proteinase, which are products of the Bmpl, TII1 and TII2 genes. BMP I (bone morphogenetic protein I) is a procollagen C-proteinase that processes the propeptide to yield a functional 30 kDa enzyme and an 18 kDa propeptide. The sequence coding for the pro-peptide is moderately (60-70%) conserved, whereas the sequence coding for the C-terminal 30 kDa region (underlined, SEQ ID NO: 3) of the proenzyme in which the active site is located is highly conserved (approximately 95%). (Kagan and Li, J. Cell. Biochem. 88:660-672 (2003); Kagan et al., J. Cell Biochem. 59:329-38 (1995)). The N-glycosyl units are also subsequently removed. LOX occurs in unprocessed and/or processed (mature) forms. The mature form of LOX is typically active although, in some embodiments, unprocessed LOX is also active.

Particular examples of a LOXL enzyme or protein are described in Molnar et al., Biochim Biophys Acta. 1647: 220-24 (2003); Csiszar, Prog. Nucl. Acid Res. 70:1-32 (2001); and in WO01/83702, all of which are herein incorporated by reference in their entirety. In the present invention, "LOXL" refers to a lysyl oxidase-like protein in general. These enzymes include LOXL1, encoded by mRNA deposited at GenBank/EMBL BC015090; AAH15090.1; LOXL2, encoded by mRNA deposited at GenBank/EMBL U89942; LOXL3, encoded by mRNA deposited at GenBank/EMBL AF282619; AAK51671.1; and LOXL4, encoded by mRNA deposited at GenBank/EMBL AF338441; AAK71934.1.

Shown below is an exemplary human LOXL1 sequence, GenBank Acc. No. AAH15090 (SEQ ID NO: 5)

52074 (2003)). LOXL2 may also be proteolytically cleaved analogously to the other members of the LOXL family and secreted (Akiri et al., Cancer Res. 63:1657-1666 (2003)).

The terms "LOX" and "LOXL" also encompass functional fragments or derivatives that substantially retain enzymatic activity catalyzing the deamination of lysyl residues. Typically, a functional fragment or derivative retains at least 50% of 60%, 70%, 80%, 90%, 95%, 99% or 100% of its lysyl oxidation activity. It is also intended that a LOX/LOXL protein can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity. See, e.g., Watson, et al., Molecular Biology of the Gene, 4th Edition, 1987, The Benjamin/Cummings Pub. Co., p. 224. Conservative and non-conservative amino acid substitutions have been described above.

As used herein, the term "conservative sequence modifications" refers to amino acid modifications that do not significantly affect or alter the activity of a LOX or LOXL. Conservative amino acid substitutions are ones in which the amino acid residue is replaced with an amino acid residue having a similar side chain. Families of amino acid residues having similar side chains have been defined in the art.

Amino acid substitutions can be made, in some cases, by selecting substitutions that do not differ significantly in their effect on maintaining (a) the structure of the peptide backbone in the area of the substitution, (b) the charge or hydrophobicity of the molecule at the target sit; or (c) the bulk of the side chain. For example, naturally occurring

```
  1    malargsrql galvwgaclc vlvhgqqaqp gqgsdparwr qliqwenngq vysllnsgse 61    yvpagpqrse sssrvllaga pqaqqrrshg sprrrqapsl plpgrvgsdt vrgqarhpfg 121    fgqvpdnwre vavgdstgma rartsvsqqr hggsassvsa safastyrqq psypqqfpyp 181    qapfvsqyen ydpasrtydq gfvyyrpagg gvgagaaava sagviypyqp raryeeyggg 241    eelpeyppqg fypaperpyv pppppppdgl drryshslys egtpgfeqay pdpgpeaaga 301    hggdprlgwy ppyanpppea ygppralepp ylpvrssdtp ppggerngaq qgrlsvgsvy 361    rpnqngrglp dlvpdpnyvq astyvgrahl yslrcaaeek clastayape atdydvrvll 421    rfpqrvknqg tadflpnrpr htwewhschq hyhsmdefsh ydlldaatgk kvaeghkasf 481    cledstcdfg nlkryactsh tqglspgcyd tynadidcqw iditdvqpgn yilkvhvnpk 541    yivlesdftn nvvrcnihyt gryvsatnck ivqs
```

Similar potential signal peptides as those described above for LOX have been predicted at the amino terminus of LOXL, LOXL2, LOXL3, and LOXL4. The predicted signal cleavage sites are between Gly25-Gln26 for LOXL, between Ala25-Gln26, for LOXL2, and between Gly25-Ser26 for LOXL3. The consensus for BMP-1 cleavage in pro-collagens and pro-LOX is between Ala/Gly-Asp, and often followed by an acidic or charged residue. A potential cleavage site to generate active LOXL is Gly303-Asp304, however, it is then followed by an atypical Pro. LOXL3 also has a potential cleavage site at Gly447-Asp448, which is followed by an Asp, processing at this site may yield an active peptide of similar size to active LOX. A potential cleavage site of BMP-I was also identified within LOXL4, at residues Ala569-Asp570 (Kim et al., J. Biol. Chem. 278:52071- residues can be divided into groups based on side-chain properties; (1) hydrophobic amino acids (norleucine, methionine, alanine, valine, leucine, and isoleucine); (2) neutral hydrophilic amino acids (cysteine, serine, threonine, asparagine, and glutamine,); (3) acidic amino acids (aspartic acid and glutamic acid); (4) basic amino acids (histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Examples of substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. Exemplary substitutions are shown in the table below. Amino acid substitutions may be introduced into human LOX/LOXL and the products screened for retention of the biological activity of human LOX/LOXL.

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

A major regulator of tendon mechanical properties (10, 12), LOX oxidatively deaminates lysine and hydroxylysine residues of collagen molecules to facilitate crosslink formation between adjacent collagen molecules (13). In addition, LOX also affects elastin to crosslink elastin. As shown in this invention, inhibition of LOX activity via β-aminopropionitrile (BAPN) reduced both LOX-mediated crosslink density and tendon modulus during tissue formation without affecting collagen content or organization. Notably, statistical analysis showed modulus correlated with crosslink density ($r^2$=0.80, $p<0.0001$) with and without perturbation of LOX activity (12).

Furthermore, study was carried out to understand the role of embryo movement in regulating mechanical property development of calcaneal tendons and whether LOX is involved in this process. It was hypothesized that perturbation of chick embryo movement activity during later developmental stages alters LOX activity and that this leads to changes in tendon mechanical properties. Paralysis (zero movement frequency) and hypermotility (increased movement frequency) led to decreases and increases in elastic modulus, respectively. Furthermore, LOX activity was downregulated with paralysis, and inhibition of LOX during hypermotility abrogated modulus increases that occurred with hypermotility alone. Taken together, mechanical loading of tendon during development is critical for the development of mechanical properties and may require the involvement of LOX. The findings disclosed herein establish new insights into the role of embryo movement in musculoskeletal tissue development and how the LOX enzyme may be involved in mechanical regulation of tendon development.

The chick embryo is a well-established model to study development of musculoskeletal tissues, sharing significant similarities with mammals (10, 12, 20-27). Notably, the LOX amino acid sequence is highly conserved across human, mouse, rat, and chicken (16). Additionally, unlike mammals, the chick embryo can be manipulated in ovo and independently of maternal influences. Injecting DMB and 4-AP into the air pocket likely affected various tissues throughout the chick embryo. The multiple perturbations in the study disclosed herein collectively and compellingly suggest that altered embryo movement frequency was the major contributor to changes in elastic modulus of the calcaneal tendons. Localizing drug treatments to only the leg and testing different DMB and 4-AP dosages as well as different kicking frequencies can be carried out. Complementary studies using an in vitro bioreactor system (28-30) could impose more highly controlled strains, strain rates, and frequencies on explant tendons.

Cells

Collagen-producing cells, elastin-producing cells, and/or progenitor cells thereof can be employed in this invention, which provides collagens or elastin or both for the integrated growth, differentiation, and regeneration of tissue capable of substantially functioning as, e.g., tendon, ligament, cartilage, or bone. The cells can be administered directly to a site of an injured tissue or be part of an implant or construct to be implanted. By forming an integrated construct in the shape of a tissue (e.g., a ligament or a joint) outside the body, the implant can adhere to the surface of the ligament or joint and integrate appropriately. As would be readily apparent to one of skill in the art, progenitor cell types, such as mesenchymal stem cells, primary chondrocytes, or osteoblasts are useful for these applications.

The cells can be autologous, allogeneic or xenogeneic with respect to a host, preferably the cells are autologous. Conveniently, examples of the cells can be chondrocytes, fibrochondrocytes, fibroblasts, osteoblasts, or sub-populations thereof, which have a differentiated phenotype. Alternatively, precursors of the aforementioned cell types may be used which have the potential to differentiate into such cells.

In some embodiments, the cells used in conjunction with the methods of the present disclosure may be derived from mesenchymal, embryonic, induced pluripotent stem cells, skin cells, or other stem cells. The cells may be derived from any source and site for obtaining a cell sample comprising a sufficient number of cells to produce a collagenous tissue. Such cells and cell samples may be obtained by any means suitable for obtaining a cell sample comprising a sufficient number of cells. In certain embodiments, such a means may comprise enzymatic digestion of native tissue. Suitable enzymes for such an enzymatic digestion include, but are not limited to, one or more collagenases.

The presently disclosed implantable composition can comprise one or more cells that can develop into a suitable replacement of a target tissue (e.g., tendon, ligament, cartilage, or bone). Particularly, the one or more cells comprise, or are derived from, a precursor cells, such as but not limited to a stem cell.

As used herein, the term "stem cell" refers to any unipotent, multipotent, pluripotent and/or totipotent cell that can be differentiated into a desired lineage. As such, the presently disclosed subject matter can employ stem cells that can be differentiated into a tissue appropriate for replacement of native pathological tissues. Representative stem cells include embryonic stem (ES) cells, embryonic germ (EG) cells (e.g., pluripotent cells derived from primordial germ cells), and somatic stem cells (alternatively referred to herein as "adult stem cells").

In some embodiments, the one or more cells described herein comprise an adult stem cell. Adult stem cells can be derived from various adult tissues including, but not limited to liver, bone marrow, umbilical cord blood, brain, peripheral blood, blood vessels, skeletal muscle, adipose tissue, and skin. Methods for the isolation, culturing, and manipulation of adult stem cells from various sources can be found in U.S. Pat. Nos. 6,242,252 and 6,872,389 (hepatic stem cells); U.S. Pat. No. 6,387,367 (hematopoietic/mesenchymal stem cells); Kogler et al. (2004) J Exp Med 200:123-135 (placental cord blood); Williams et al. (1999) The American Surgeon 65:22-26 (skeletal muscle); U.S. Pat. No. 6,777,231 (adipose tissue); and Blanpain et al. (2004) Cell 118:635-648 (skin), the entire contents of each of which are hereby incorporated in their entireties.

Representative techniques for deriving, growing, and manipulating ES cells and EG cells are disclosed in the following publications: Evans and Kaufman (1981) Nature 292:154-156; Martin (1981) Proc Natl Acad Sci USA 78:7634+7638; Robertson (1986) Trends Genet 2:9-13; PCT International Patent Application Publications WO 96/22362; WO 97/32033; and WO 98/43679; and U.S. Pat. Nos. 6,200,806; 6,090,622; 5,843,780; 5,690,926; 5,670,372; and 5,453,357; and references therein, all of which are incorporated by reference herein in their entireties.

In some embodiments, the cells can be genetically modified, e.g., to express exogenous genes or to repress the expression of endogenous genes. In some embodiments, the present invention provides methods of genetically modifying such cells and populations. In accordance with these methods, the cells can be exposed to an expression construct comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode a biologically active (e.g., functional) fragment of a protein.

Thus, for example, the coding polynucleotide can encode a LOX/LOXL, a gene conferring resistance to a toxin, a hormone (such as peptide growth hormones, hormone releasing factors, sex hormones, adrenocorticotrophic hormones, cytokines (e.g., interferins, interleukins, lymphokines), etc.), a cell-surface-bound intracellular signaling moiety (e.g., cell adhesion molecules, hormone receptors, etc.), a factor promoting a given lineage of differentiation, etc. Of course, where it is desired to employ gene transfer technology to deliver a given transgene, the sequence will be known. In some embodiments, the coding polynucleotide encodes a growth factor. In some embodiments, the coding polynucleotide encodes a LOX/LOXL, a LOX/LOXL enhancer (e.g., BMP-1) or a functional fragment thereof.

The cells can be stably or transiently transfected or transduced with a nucleic acid of interest using a plasmid, viral or alternative vector strategy. With respect to the cells, nucleic acids of interest include, but are not limited to, those encoding gene products which enhance the production of extracellular matrix components found in tendon, ligament, or cartilage, such as collagen, TGF-β, BMP, activin and insulin-like growth factor.

Thus, in some embodiments, the transduction of regulatory genes into the cells, for example stem cells, can be performed with viral vectors (adenovirus, retrovirus, adeno-associated virus, or other vector) purified by cesium chloride banding or any other well-known method at a multiplicity of infection (viral units:cell) of between 10:1 to 2000:1. Cells can be exposed to the virus in serum-free or serum-containing medium in the absence or presence of a cationic detergent such as polyethyleneimine or LIPOFECTAMINE (IN-VITROGEN, Carlsbad, Calif., United States of America) for a period of 1 hour to 24 hours (Byk et al. (1998) Human Gene Therapy 9:2493-2502; Sommer et al. (1999) Calcif. Tissue Int. 64:45-49) or in three-dimensional cultures by incorporation of the plasmid DNA vectors directly into a biocompatible polymer (Bonadio et al. (1999) Nat. Med. 5:753-759).

In some embodiments, cells, for example stem cells, are transfected with the gene to be expressed to produce cells having stably incorporated therein the DNA encoding the molecules to be expressed. Stable transfections can be obtained by culturing and selecting for expression of the desired encoded molecules. In some embodiments, the cells that exhibit stable expression can be seeded onto or into the appropriate fiber matrix and implanted in a subject. For the tracking and detection of functional proteins encoded by these genes, the viral or plasmid DNA vectors can contain a readily detectable marker gene, such as the green fluorescent protein (GFP) or β-galactosidase enzyme, both of which can be tracked by histochemical means.

Within the expression cassette, the coding polynucleotide can be operably linked to a suitable promoter. Examples of suitable promoters include prokaryotic promoters and viral promoters (e.g., retroviral inverted terminal repeats (ITRs), long terminal repeats (LTRs), immediate early viral promoters (IEp), such as herpes virus IEp (e.g., ICP4-IEp and ICP0-IEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit β-globin regulatory elements), constitutively active promoters (e.g., the β-actin promoter, etc.), signal specific promoters (e.g., inducible promoters such as a promoter responsive to RU486, etc.), and tissue-specific promoters. It is well within the skill of the art to select a promoter suitable for driving gene expression in a pre-defined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene can be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpes viruses, lentiviruses, papillomaviruses, retroviruses, etc.). Any method of constructing the desired expression cassette within such vectors can be employed, many of which are well known in the art (e.g., direct cloning, homologous recombination, etc.). Of course, the choice of vector will largely determine the method used to introduce the vector into the cells (e.g., by protoplast fusion, calcium-phosphate precipitation, gene gun, electroporation, infection with viral vectors, etc.), which are generally known in the art.

In some embodiments, the genetically altered cells can be employed as bioreactors for producing the product of the transgene. In some embodiments, the genetically modified cells are employed to deliver the transgene and its product to a subject. For example, the cells, once genetically modified, can be introduced into the subject under conditions sufficient for the transgene to be expressed in vivo.

Thus, the present invention also provides in some embodiments methods for treatment of tendon, ligament or joint disorders. Disclosed herein are approaches for regenerating collagen-containing tissues. Further disclosed herein is the use of progenitor, stem, or primary cells in conjunction with a composition that comprises a medium capable of supporting the growth and differentiation of the cells into functional tissue, but not necessarily recapitulating the native structure of the tissue.

Methods of Treatment and Prevention/Regenerating Injured Tissue or Component Thereof The presently disclosed methods involve the regeneration of tissue, promotion of healing of an injury (e.g., tendon or ligament injury), or enhancing healthy tissues. As disclosed herein, the methods can be used for treatment of birth defects in utero too. To that end, an embryo/fetus in need of such a treatment can be stimulated to increase one or more types of mechanical stimulation (e.g., movement-induced or other), and the LOX activity could be enhanced to improve mechanical properties of developing tissues.

The regeneration of tissue refers to the process of renewal and growth of cells and extracellular matrix components within a particular tissue that results in the production of tissue that has a cellular component and architecture that allows for the normal functions of the particular tissue type.

An injury or wound refers to damage or harm to a structure or function of the body caused by intrinsic and/or extrinsic factors. Non-limiting intrinsic or extrinsic factors that can cause an injury or wound include those of chemical, mechanical, thermal, bacterial, or physical means and encompass those that occur as the result of surgical procedures, overuse, or environmental conditions. The wound can be an open wound in which the skin is broken (e.g., lacerations, abrasions, puncture wound) or a closed wound. Particular wounds that can be treated by this invention include, but are not limited to, tendon or ligament injuries, bone injuries (e.g., complete or partial fractures), skin wounds, and skeletal muscle injuries.

Intrinsic factors that can contribute to the development of injuries to tendons and/or ligaments include genetic susceptibility, overuse, poor biomechanics, poor nutrition, and obesity. The extrinsic factors are often related to sports and include excessive forces or loading, poor training techniques, environmental conditions, and surgical procedures. The injury to the tendon and/or ligament can be a closed wound or an open wound, where the skin is lacerated, cut or punctured. The injury can include inflammation, a sprain, strain, tearing, stretching, or laceration of the tendon or ligament.

A tendon is a band of connective tissue that connects muscles to bones or cartilage. A ligament is a band of connective tissue that connects bones to other bones to form joints. Injuries to tendons include tendinitis (acute tendon injury accompanied by inflammation), tendinosis (chronic tendon injury with degeneration at the cellular level and no inflammation), and other tendinopathies exhibiting chronic tendon injury with no etiological implications. With tendinosis, damage to collagen, cells, and the vascular components of the tendon can occur, such as irregularities of collagen fibrils (e.g., disorientation, degeneration, thinning, non-uniformity in length or diameter, increase in the amount of glycosaminoglycans between the fibrils), rounded tenocytes or other cell abnormalities, and the ingrowth of blood vessels.

The healing of an injury to any type of tendon can be promoted with the invention disclosed herein, including a hand flexor tendon, a tendon within the rotator cuff, and an Achilles tendon, and within horses, a superficial digital flexor tendon (SDFT) and a deep digital flexor tendon (DDFT) of either the hindlimb(s) or forelimb(s).

Likewise, the healing of an injury to any type of ligament can be promoted with the invention disclosed herein, including an anterior cruciate ligament (ACL), posterior cruciate ligament (PCL), lateral collateral ligament (LCL), medial collateral ligament (MCL), and in horses, a suspensory ligament of either the hindlimb(s) or forelimb(s). A common ligament injury in horses that can be healed according to the presently disclosed methods is proximal suspensory desmitis, an inflammation of the suspensory ligament just below the hock.

In some embodiments the invention includes both prophylactic and therapeutic methods of (i) improving a mechanical property of a tissue or a component thereof or (ii) regenerating an injured tissue or a component thereof in a subject.

Subjects having or at risk for the condition can be identified by, for example, any one or a combination of known in the art. Administration of a prophylactic agent can occur prior to the manifestation of symptoms characteristic of the condition or decrease, such that a condition is prevented or, alternatively, delayed in its progression. Depending on the type of the condition, for example, a LOX/LOXL enhancer can be used for treating the subject.

In one aspect, the method includes increasing a level of LOX activity in the tissue by e.g., administering to the subject a LOX/LOXL enhancer, e.g., a LOX or LOXL (e.g., a LOX or LOXL polypeptide, or active fragment thereof, or a nucleic acid encoding the polypeptide or active fragment thereof), or another agent that modulates (i.e., increases) LOX or LOXL expression or at least one LOXL activity.

As used herein, an active fragment of a LOX or LOXL polypeptide retains the ability to oxidize lysine residues in elastin and collagen. For example, an active fragment can be missing a portion of the N-terminal sequence but retaining the C-terminal enzymatic domain (e.g., a fragment comprising from amino acids about 145, 179, 326, 338, to about 574, referring to the human sequence, GenBank Acc. No. AAH15090, SEQ ID NO: 5). An active fragments can include the C-terminal 28 kD of the polypeptide. Fragments can be generated by recombinant DNA techniques known in the art, or can be produced by enzymatic digestion of all or part of a full length LOX or LOXL polypeptide, e.g., digestion with bone morphogenetic protein-1 (BMP-1; see Borel et al., supra). Such fragments can comprise the N-terminal portion of the sequence that is conserved between LOX, LOXL1, LOXL2, LOXL3, and LOXL4, e.g., comprising the putative copper-binding site, the lysine tyrosylquinone cofactor formation, and/or the cytokine receptor-like domain (see, e.g., Maki, Dissertation: LYSYL OXIDASES, Cloning and Characterization of the Fourth and the Fifth Human Lysyl Oxidase Isoenzymes, and the Consequences of a Targeted Inactivation of the First Described Lysyl Oxidase Isoenzyme in Mice, Collagen Research Unit, Biocenter Oulu and Department of Medical Biochemistry and Molecular Biology, University of Oulu (2002)). Smaller or larger fragments can also be used.

In some embodiments, to modulate LOX or LOXL expression or activity (e.g., for therapeutic purposes), a cell is contacted with a LOX or LOXL nucleic acid or polypeptide (or active fragment thereof), or an agent that modulates one or more of the activities of LOX or LOXL polypeptide activity associated with the cell. An agent that modulates LOX or LOXL polypeptide activity can be, e.g., an agent as described herein, such as a nucleic acid or a polypeptide, a naturally-occurring binding partner of a LOX or LOXL polypeptide, a LOXL antibody, a LOXL agonist, a peptidomimetic of a LOXL agonist, or other small molecule. The agent can be synthetic, or naturally occurring. The cell can be an isolated cell, e.g., a cell removed from a subject or a cultured cell, or can be a cell in situ in a subject.

A LOX/LOXL enhancer agent can, in some embodiments, stimulate one or more LOX/LOXL activities. Examples of such stimulatory agents include active LOX/LOXL polypeptide or an active fragment thereof, and a nucleic acid molecule encoding a LOX/LOXL polypeptide or active fragment thereof.

As defined herein, a therapeutically effective amount of a LOX/LOXL nucleic acid or polypeptide composition is a dosage effective to treat or prevent a particular condition for which it is administered. The dose will depend on the composition selected, i.e., a polypeptide or nucleic acid. The compositions can be administered from one or more times per day to one or more times per week, including once every other day. The skilled artisan will appreciate that certain factors may influence the dosage and timing required to effectively treat a subject, including but not limited to the severity of the condition, previous treatments, the general health and/or age of the subject, and other conditions present. Moreover, treatment of a subject with a therapeutically effective amount of the therapeutic LOX/LOXL compositions of the invention can include a single treatment or a series of treatments, as well as multiple (i.e., recurring) series of treatments.

Dosage, toxicity and therapeutic efficacy of such LOX/LOXL compositions can be determined by pharmaceutical procedures known in the art in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit high therapeutic indices are preferred. While compositions that exhibit toxic side effects may be used, care should be taken to design a delivery system that targets such compositions locally to the site of affected tissue to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The invention further provides pharmaceutical compositions comprising a LOX/LOXL enhancer, for use in the treatment of conditions mentioned above. Such compositions typically include a LOX/LOXL enhancer, and a pharmaceutically acceptable carrier. A LOX/LOXL enhancer or activator refers to (i) an agent that stimulates one or more LOX/LOXL activities or (ii) a positive modulator of LOX/LOXL activity or expression The term covers agents (such as BMP-1 and Tolloid) that cleave ProLox to produce an active mature LOX. As used herein, examples of a LOX/LOXL enhancer can be a LOX/LOXL nucleic acid or polypeptide (or active fragment thereof) or other positive modulator of LOX/LOXL activity or expression, e.g., a LOX polypeptide, a pre-proLOX polypeptide, a proLOX polypeptide, a nucleic acid encoding said LOX/pre-proLOX polypeptide/proLOX polypeptide, a viral particle having said nucleic acid, an engineered cell expressing said LOX, pre-proLOX, or proLOX polypeptide, BMP-1, Fibronectin, Tolloid, Copper, Vitamin B6, Ascorbic acid, and Procollagen c proteinase.

As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A LOX/LOXL enhancer pharmaceutical composition is formulated to be compatible with its intended route of administration. Examples of routes of administration include parenteral (e.g., intravenous, intradermal, or subcutaneous), oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

LOX/LOXL enhancer pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active LOX/LOXL enhancer in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation are vacuum drying and freeze-drying which yields a powder of the active ingredient plus any additional desired ingredient from a previously sterile-filtered solution thereof.

Oral LOX/LOXL enhancer compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the LOX/LOXL enhancer can be delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of a LOX/LOXL enhancer can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, compositions comprising a LOX/LOXL enhancer for transdermal application can further comprise cosmetically acceptable carriers or vehicles and any optional components. A number of such cosmetically acceptable carriers, vehicles and optional components are known in the art and include carriers and vehicles suitable for application to skin (e.g., sunscreens, creams, milks, lotions, masks, serums, etc.), see, e.g., U.S. Pat. Nos. 6,645,512 and 6,641,824. In particular, optional components that may be desirable include, but are not limited to absorbents, anti-acne actives, anti-caking agents, anti-cellulite agents, anti-foaming agents, anti-fungal actives, anti-inflammatory actives, anti-microbial actives, anti-oxidants, antiperspirant/deodorant actives, anti-skin atrophy actives, anti-viral agents, anti-wrinkle actives, artificial tanning agents and accelerators, astringents, barrier repair agents, binders, buffering agents, bulking agents, chelating agents, colorants, dyes, enzymes, essential oils, film formers, flavors, fragrances, humectants, hydrocolloids, light diffusers, nail enamels, opacifying agents, optical brighteners, optical modifiers, particulates, perfumes, pH adjusters, sequestering agents, skin conditioners/moisturizers, skin feel modifiers, skin protectants, skin sensates, skin treating agents, skin exfoliating agents, skin lightening agents, skin soothing and/or healing agents, skin thickeners, sunscreen actives, topical anesthetics, vitamin compounds, and combinations thereof.

The LOX/LOXL enhancer compositions can also be prepared in the form of suppositories (e.g., with conventional suppository bases such as cocoa butter and other glycerides) or retention enemas for rectal or vaginal delivery. Such suppositories can be used particularly for the treatment of conditions associated with the loss of in elastic fibers that affect the pelvic organs, e.g., pelvic organ prolapse and/or urinary incontinence, inter alia.

LOX/LOXL enhancer compositions comprising nucleic acids can also be administered by any method suitable for administration of nucleic acid agents. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol. 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, LOX/LOXL enhancer compositions are prepared with carriers that will protect against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using techniques known in the art. The materials can also be obtained commercially, e.g., from Alza Corporation and Nova Pharmaceuticals, Inc. Liposomal suspensions (including liposomes targeted to specific cells with monoclonal antibodies) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration for the treatment or prevention of a condition as mentioned above.

Administration of the compositions described above can be carried out by any method known to one of ordinary skill in the art. In some embodiments, suitable methods for administration of the compositions of the presently disclosed subject matter include, but are not limited to injection into the target tissue or target site. The term "target tissue" as used herein refers to an intended site for engraftment following administration to a subject.

In some embodiments, the compositions comprise cells present in a matrix (e.g., a gel) within the pores of a fiber scaffold. The fiber scaffold can be implanted at a predetermined site (i.e., a ligament, a tendon, or a joint) to replace, repair, and/or restore a target tissue and/or structure at the particular site of insertion. In some embodiments, the fiber scaffold can be implanted in a subject to alleviate tissue loss, damage, injury, or combinations thereof.

The fiber scaffolds can be implanted into the subject at the site in need of treatment using standard surgical techniques. In some embodiments, the fiber scaffold is constructed, seeded with cells and cultured in vitro prior to implantation. The cells can be cultured in the device, tested for viability, and then implanted. In some embodiments, the fiber scaffold is constructed, seeded with cells and cultured in vivo after or during implantation. In some embodiments, the scaffold is implanted without cells. In some embodiments, the fiber scaffolds can be used for delivery of multiple different cell types. The scaffold can be implanted in one or more different areas of the body to suit a desired application.

In addition, there are situations where it could be desirable to use more than one matrix, each implanted at the most optimum time for growth of the attached cells to form a functioning three-dimensional structure from the different matrices.

An effective dose of a composition of the presently disclosed subject matter is administered to a subject in need thereof. An "effective amount" or a "therapeutic amount" is an amount of a therapeutic composition sufficient to produce a biologically or clinically relevant response in a subject being treated. The actual amount of a therapeutic agent in the composition can be varied so as to achieve the desired therapeutic response for a particular subject. The selected dosage level will depend upon several factors including, but not limited to the ability of the cells or their progeny to engraft the target tissue, the route of administration, combination with other drugs or treatments, the severity of the condition being treated, and the condition and prior medical history of the subject being treated.

The potency of a composition can vary, and therefore an "effective amount" can vary. However, using standard assay methods, one skilled in the art can readily assess the potency and efficacy, and adjust the therapeutic regimen accordingly. In view of the disclosure of the present invention, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

The subjects treated in the present invention are in some embodiments human subjects, although it is to be understood that the presently disclosed subject matter is effective with respect to all vertebrate animals, including mammals, which are intended to be included in the term "subject". Moreover, a mammal is understood to include any mammalian species in which treatment or prevention of a disease is desirable, particularly agricultural and domestic mammalian species.

Kits

The disclosure also provides kits, where the kits include one or more components employed in methods of the invention, e.g., LOX/LOXL enhancers (such as a LOX polypeptide, a pre-proLOX polypeptide, a proLOX polypeptide, a nucleic acid encoding said LOX, pre-proLOX, or proLOX polypeptide, a viral particle having said nucleic acid, an engineered cell expressing said LOX, pre-proLOX, or proLOX polypeptide, BMP-1, Fibronectin, Tolloid, Copper, Vitamin B6, Ascorbic acid, and Procollagen c proteinase), vectors, and cells, as described herein. Kits may also include tubes, buffers, packaging materials, etc., and instructions for use. The various reagent components of the kits may be present in separate containers, or some or all of them may be pre-combined into a reagent mixture in a single container, as desired.

In addition to the above components, the kits may further include instructions for practicing the subject methods. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), hard drive etc., on which the information has been recorded. Yet another form of these instructions that may be present is a website address which may be used via the internet to access the information at a removed site.

Definitions

As used herein, "mechanical stimulation or loading" shall mean forces applied to a structure or a component which are mechanical in nature, or a mechanical force. In one aspect, the mechanical loading can be compression. In another aspect, the mechanical loading can be tension.

The term "collagen" as used herein refers to a group of naturally occurring proteins found in the flesh and in connective tissues of mammals. It is the main component of connective tissue, and is the most abundant protein in mammals, making up about 25% to 35% of the whole-body protein content. Collagen, in the form of elongated fibrils, is mostly found in fibrous tissues, such as tendon, ligament, and skin, and is also abundant in cornea, cartilage, bone, blood vessels, the gut, and intervertebral disc. So far, 29 types of collagen have been identified and over 90% of the collagen in the body is of type I (skin, tendon, vascular, ligature, organs, bone), type II (cartilage), type III (reticulate (main component of reticular fibers), and type IV (which forms the bases of cell base membrane).

As used herein, "treatment" means the application or administration of a LOX or LOXL1 enhancer therapeutic agent to a subject (e.g., a human or a veterinary or experimental animal subject), or application or administration of a therapeutic agent to an isolated tissue or cell line from a subject, who has a condition, a symptom of condition, or a predisposition to get a condition, with the purpose to cure, heal, alleviate, relieve, alter, remedy, ameliorate, improve, prevent, or affect the disease, symptoms of the condition, or the predisposition to get the condition. A LOX or LOXL1 enhancer therapeutic agent includes, but is not limited to, small molecules including peptidomimetics, peptoids, nucleic acids (e.g., nucleic acids encoding a LOX or LOXL polypeptide or active fragment thereof), aptamers, carbohydrates, polysaccharides, non-nucleic acid small organic molecules, inorganic molecules, polypeptides, antibodies, ribozymes, and drugs.

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation).

A conservative modification or functional equivalent of a peptide, polypeptide, or protein disclosed in this invention refers to a polypeptide derivative of the peptide, polypeptide, or protein, e.g., a protein having one or more point mutations, insertions, deletions, truncations, a fusion protein, or a combination thereof. It retains substantially the activity to of the parent peptide, polypeptide, or protein (such as those disclosed in this invention). In general, a conservative modification or functional equivalent is at least 60% (e.g., any number between 60% and 100%, inclusive, e.g., 60%, 70%, 75%, 80%, 85%, 90%, 95%, 96%, 97%, 98%, and 99%) identical to a parent (e.g., SEQ ID NO: 1, 3, 4, or 5).

A nucleic acid or polynucleotide refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the protein of this invention. For this purpose, one can operatively linked the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector includes a nucleic acid in a form suitable for expression of the nucleic acid in a host cell. Preferably the vector includes one or more regulatory sequences operatively linked to the nucleic acid sequence to be expressed.

A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein or RNA desired, and the like. The expression vector can be introduced into host cells to produce a polypeptide of this invention. A promoter is defined as a DNA sequence that directs RNA polymerase to bind to DNA and initiate RNA synthesis. A strong promoter is one which causes mRNAs to be initiated at high frequency.

The term "operably-linked" or "operably-linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a polypeptide will typically have its own operably linked promoter sequence.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions.

As used herein, the percent homology between two amino acid sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, known in the art.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder. The terms "prevent," "preventing," "prevention," "prophylactic treatment" and the like refer to reducing the probability of developing a disorder or condition in a subject, who does not have, but is at risk of or susceptible to developing a disorder or condition.

An effective amount refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment.

The term "pharmaceutical composition" refers to the combination of an active agent with a carrier, inert or active, making the composition especially suitable for diagnostic or therapeutic use in vivo or ex vivo.

A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

A "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

Musculoskeletal conditions, diseases and disorders are abnormal conditions of muscles and their associated ligaments, tendons, connective tissues and bones. The causes of musculoskeletal conditions may include, but are not limited to, wear and tear from daily activities, trauma to an area, auto accidents, falls, fractures, sprains, dislocations, direct blows to muscles, postural strain, repetitive movements, overuse and prolonged immobilization and disease related conditions. Examples include an injury or pain in the body's bones, joints, ligaments, muscles, tendons, nerves, tendons, cartilages and structures that support limbs, neck and back, which is a degenerative disease and inflammatory condition that causes pain and impair normal activities. Examples of specific musculoskeletal disorders include all diseases related to bones, joints, ligaments, muscles, nerves, tendons, cartilages and structures that support limbs, neck and back. The musculoskeletal disorder can be selected from the group consisting of sprains, strains and tears of ligaments, tendons, muscles and cartilage, tendonitis, tenosynovitis, fibromyalgia, osteoarthritis, rheumatoid arthritis, polymyalgia rheumatica, bursitis, acute and chronic back pain, osteoporosis, carpal tunnel syndrome, DeQuervains's disease, trigger finger, tennis elbow, rotator cuff, ganglion cysts, osteogenesis imperfecta, Duschennes, Hurler's and Hunter's syndromes and combination thereof.

As used herein, the term "mesenchymal stem cells" or "MSCs" refers to multipotent stem cells, which can differentiate into a variety of cell types, including for example, osteoblasts, chondrocytes and adipocytes etc. The mesenchymal stem cells or MSCs may be derived from any tissue sources, including but not limited to bone marrow tissues, adipose tissue, muscle tissue, corneal stroma or dental pulp of deciduous baby teeth, umbilical cord tissues or umbilical cord blood etc. In one example of the invention, the MSCs are bone marrow MSCs.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

EXAMPLES

Example 1

This example describes material and methods used in Examples 2-5 below. All materials and reagents were obtained from THERMOFISHER (MA, USA) unless otherwise noted.

Chick Embryo Culture and Injections

Fertilized white leghorn eggs (University of Connecticut poultry farm) were incubated at 37° C. under high humidity. For developmental characterizations, eggs were not injected. For other experiments, a single dose of sterile saline (control), 0.2% DMB (rigid paralysis), 0.2% pancuronium bromide (PB) (flaccid paralysis), 0.2% 4-AP (hypermotility), or 0.2% 4-AP and 5 mg BAPN per gram of embryo dry mass (to simultaneously induce hypermotility and inhibition of LOX activity) was injected at the air sac end of an HH43 egg and incubated for another 48 h, as previously described (10). DMB dosage was based on previous studies that paralyzed the embryo without affecting gross development (3). 4-AP dosage was based on previous studies that showed a single injection induced hypermotility up to 400% in HH36 to HH44 chick embryos for at least 24 h (14). At specific timepoints, chick embryos were sacrificed by decapitation and staged based on anatomical features (15). The calcaneal tendon was homogenized in TRIzol LS reagent, snap frozen for protein and enzyme assays, or embedded for cryosectioning.

Leg Explant Culture

Lower limbs were isolated from anatomically staged HH43 chick embryos and cultured in growth medium (Dulbecco's Modified Eagle's Medium, 10% fetal bovine serum, 1% antibiotic/antimycotic) supplemented with saline or 0.2% DMB. Media were changed after 24 h. Calcaneal tendons were harvested for LOX activity assay after 48 h.
Total RNA Isolation and Reverse Transcription Polymerase Chain Reaction (RT-PCR)

Total RNA was extracted from TRIZOL LS-preserved samples and RT-PCR was performed using SUPERSCRIPT III One-Step RT-PCR System with Platinum Taq High Fidelity DNA Polymerase (INVITROGEN, CA) with primer pairs for LOX, LOX-like (LOXL) 1 through 4, and 18S (Table 1). Product bands in the gel were analyzed using fluorescence intensity-based densitometry quantification with IMAGEJ (NIH, Bethesda, MD).

TABLE 1

Primer sequences.

| Gene | Forward | SEQ ID NO: | Reverse | SEQ ID NO: |
|---|---|---|---|---|
| LOX | TCGGGCGGATGTTAGAGACT | 6 | AGCTGGCGTCTAACAAGTCA | 7 |
| LOXL1 | TGCTACGACACCTACAACGC | 8 | GTGGTTTTGGGCTCATGGTG | 9 |
| LOXL2 | CAATTCCTTGCATCCCCAACC | 10 | TAGGGCCAGGAATGCTCAGA | 11 |
| LOXL3 | AGTTGGCACACTCGTACCG | 12 | CATCTTCACACCAACGACATCCT | 13 |
| LOXL4 | TGCGATGATGGCTTCGACTT | 14 | CTGGCCGTAAGTAGCACTGT | 15 |
| 18S | AACGGGGCCATGATTAAGAGG | 16 | TTGCGCCGGTCCAAGAATTT | 17 |

Protein and Enzyme Activity Assays

Western blot to semi-quantitatively measure proLOX levels was performed with rabbit anti-proLOX antibody or rabbit anti-β-actin antibody (ABCAM, MA). ProLOX and β-actin levels were quantified by densitometry at ~50 kDa and ~40 kDa molecular bands, respectively. LOX activity of each sample was measured using a LOX activity assay kit (ABCAM, MA). Recombinant LOXL2 enzyme (R&D Systems, MN) was used as a positive control for each assay.

Cryopreservation and Cryosectioning

Calcaneal tendons of staged embryos were cryoembedded as previously described (10) and cryosectioned at 50 μm thickness.

Two Photon Microscopy and Image Analysis

Tendon cryosections were immersed in $Ca^{2+}/Mg^{2+}$-free phosphate buffered saline (PBS) to remove O.C.T. A 20× water objective imaged a 220×220 μm region in the center of tendon midsubstance in PBS. Collagen was characterized by F-SHG at 800 nm excitation, and signal was collected by a photomultiplier tube using a 405DF30 filter. Background was determined with laser off. Background was subtracted from each F-SHG image using MATLAB (MATHWORKS, MA) and then average pixel intensities of each image were calculated to assess collagen content per unit area. Prior study showed that this measurement of collagen content correlated highly with hydroxyproline content measured with biochemical assays (12).

AFM

Force volume-AFM was used to characterize tendon elastic modulus using previously established methods (10). Briefly, tendon cryosections were immersed in PBS to remove O.C.T. A silicon nitride tip probe (~20 nm radius) with a spring constant of 0.06 N/m (BRUKER, CA) was used on an MFP-3D AFM (ASYLUM RESEARCH, CA) to obtain force curves in a 64×64 2-dimensional array over a 10 μm×10 μm tissue region in the center of the tendon midsubstance with a 1.0 μm indentation trigger point. The sample was indented at 6 μm/s, at which tendon elastic properties were previously characterized with negligible viscous effects (10). Elastic modulus was calculated by fitting force displacement curves at each indentation to the Hertzian model using equations adapted from a previous study (10).

Statistical Analysis

For RT-PCR, tendons from both legs each from at least three embryos (N≥3) were characterized. For western blot and LOX activity assays, tendons from both legs from at least three embryos (HH41 and earlier) or two embryos (HH42 and later) were pooled and five pools (N=5) were characterized. For two photon imaging and AFM, tendons from one leg each from at least five embryos (N≥5) were characterized based on a previous study (10). F-SHG was used to image three non-overlapping regions (see Two photon microscopy and image analysis section above) in the midsubstance of each tendon. AFM was used to indent one region (see AFM section above) with apparent tendon fibrillar structure in the midsubstance of each tendon. One-way ANOVA was performed for comparison of LOX family mRNA levels, proLOX levels, LOX activity levels among different developmental stages, and average stages of saline-, DMB-, 4-AP-, and 4-AP+BAPN-treated HH43 chick embryos at harvest after 48 h of treatment (α=0.05). Tukey's post-hoc test was used to perform multiple comparison analysis to evaluate the statistical differences between two specific groups at the same timepoint. Two-sample t-test was performed to compare elastic moduli, collagen content, and LOX activity levels between treatment conditions (a=0.05). All analyses were performed with GRAPHPAD PRISM v.7.0a (La Jolla, CA).

Example 2 Tendon Elastic Modulus was Affected by Embryo Movement

DMB treatment of HH43 chick embryos resulted in paralysis and significantly reduced calcaneal tendon modulus relative to controls (FIG. 1A). 4-AP treatment induced hypermotility and significantly upregulated tendon modulus relative to controls (FIG. 1A). Neither treatment affected collagen content or apparent organization relative to controls (FIGS. 1B and 1C).

Example 3 LOX Levels Increase During Development Whereas LOXL1-4 Levels do not

LOX mRNA expression levels of HH41 through HH45 tendons were higher than that of HH39 (FIG. 2A). LOXL1 mRNA maintained relatively constant levels until decreasing at HH45 (FIG. 2B). LOXL2 levels decreased from HH38 through HH45 (FIG. 2C). LOXL3 mRNA levels showed no changes between stages (FIG. 2D). LOXL4 mRNA levels decreased from HH38 to HH39 and then remained constant through HH45 (FIG. 2E).

ProLOX levels increased significantly from HH38 to HH42 and then plateaued (FIG. 3A). LOX activity levels were constant from HH38 to HH42 and then increased from HH42 through HH45 (FIG. 3B).

Example 4 LOX Activity Levels were Affected by Embryo Movement

Figures 4A, 4B:
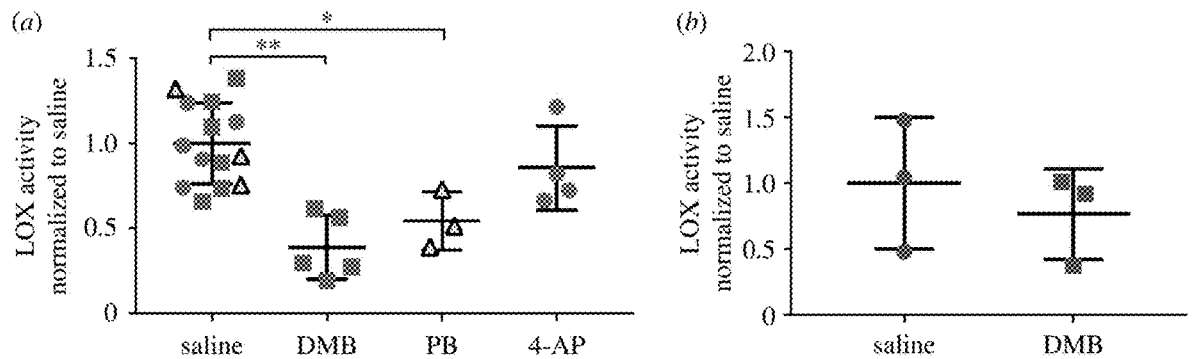
FIGS. 4A and 4B are a set of diagrams showing DMB and 4-AP effects on LOX activity levels of HH43 calcaneal tendons after 48 h (N≥3). (a) Paralytic agents DMB and pancuronium bromide (PB) treatment each decreased LOX activity levels. 4-AP treatment had no effect on LOX activity levels. (b) DMB treatment of isolated leg explants in vitro had no effect on LOX activity levels. (*p<0.05; **p<0.01).

DMB treatment of HH43 embryos significantly reduced LOX activity levels in calcaneal tendons (FIG. 4A). PB treatment to induce flaccid paralysis resulted in calcaneal tendons with significantly lower LOX activity levels than controls (FIG. 4A). In contrast, 4-AP treatment had no effects on LOX activity levels compared to controls (FIG. 4A). LOX activity levels of calcaneal tendons of leg explants cultured with DMB were similar to controls (FIG. 4B).

Figure 5:
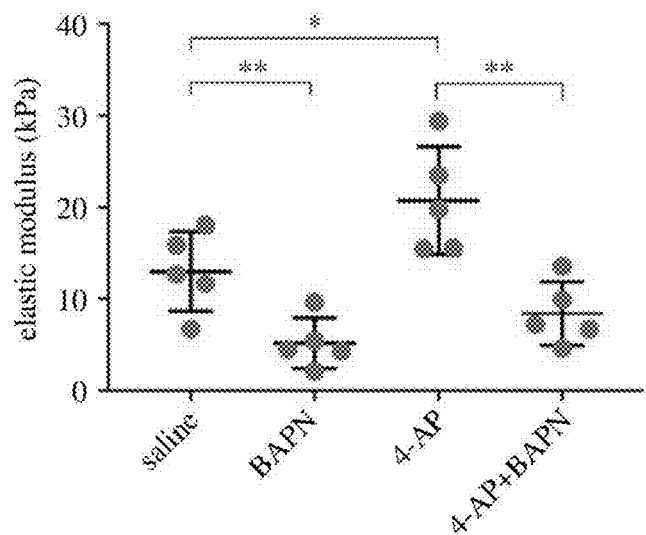
FIG. 5 is a diagram showing calcaneal tendon elastic moduli of HH43 chick embryos treated for 48 h (N=5). BAPN treatment decreased modulus relative to saline controls (same saline control data as in FIG. 1A); 4-AP treatment increased modulus relative to saline controls (same data as in FIG. 1a); 4-AP+BAPN treatment reduced modulus compared with 4-AP treatment alone. (*p<0.05, **p<0.01).

Example 5 Perturbation of LOX Activity Abrogated Hypermotility-Induced Increases in Modulus 4-AP treatment led to higher calcaneal tendon modulus than controls (FIG. 5). In contrast, 4-AP+BAPN treatment resulted in significantly lower modulus compared to 4-AP treatment alone, but was similar to controls. BAPN treatment alone reduced modulus relative to controls.

Example 6 Gross Development was Minimally Affected by Treatments

Figure 6:
FIGS. 6A, 6B, 6C, 6D, 6E, and 6F are a set of photographs showing embryos were injected at HH43, harvested after 48 h, and staged on the basis of anatomical features in comparison with non-injected HH45 embryos (N≥6). Representative legs from (a) non-injected HH45 embryo; and (b) saline-treated; (c) DMB-treated, with hyperextended digits under 'rigid paralysis'; (d) 4-AP-treated; (e) 4-AP+BAPN-treated; and (f) BAPN-treated HH43 embryos. (Scale bar: 10 mm; *p<0.05).

HH43 chick embryos treated with saline, DMB, 4-AP, and BAPN for 48 h exhibited similar anatomical features as non-injected HH45 chick embryos, reflecting normal development (Table 3). In contrast, chick embryos treated with 4-AP+BAPN staged to HH44 (Table 3). Grossly, legs harvested from saline-, 4-AP-, and 4-AP+BAPN-, and BAPN-treated embryos appeared similar to non-injected HH45 legs (FIGS. 6A, 6B, 6D, 6E, and 6F). DMB-treated chick embryos were still in rigid paralysis and possessed hyper-extended digits at 48 h (FIG. 6C).

In the above examples, assays were carried out to test the hypothesis that embryo movement frequency regulates tendon mechanical property development, focusing on HH43, when the embryo has formed functional muscles and tendons and is kicking at the highest frequency during development (11). HH43 chick embryos were treated with DMB to induce paralysis (zero frequency movement), saline (normal frequency movement), and 4-AP to induce hypermotility (high frequency movement). Elastic modulus of calcaneal tendons decreased with paralysis and increased with hypermotility, relative to controls (FIG. 1A), demonstrating movement can regulate the development of tendon mechanical properties. In addition, paralysis led to reductions in LOX activity levels (FIG. 4A), implicating LOX as an important player in normal movement-regulated development of tendon mechanical properties. Changes in LOX activity were not detected after 48 h of hypermotility, however inhibition of LOX activity during hypermotility abrogated the increases observed with hypermotility alone (FIG. 5), suggesting LOX may also be involved in mechanical upregulation of tendon mechanical properties. Taken together, these findings demonstrate movement critically regulates tendon mechanical property development and implicate LOX in this process.

These findings are significant because relatively little was known about the role of mechanics in tendon development. In previous studies, DMB treatment of HH24 chick embryos for 72 h diminished tendon marker expression in forelimb zeugopod and digits (6). DMB-induced paralysis of HH35 chick embryos also led to altered Tenascin-C protein distribution patterns by HH39 (3). These studies showed that movement is important for tendon marker expression and patterning during earlier developmental stages. However, the role of mechanics in regulating tendon development at later stages had not been studied.

(a) Tendon Elastic Modulus is Affected by Paralysis and Hypermotility

DMB irreversibly binds to acetylcholine receptors in the motor end plate to trigger an immediate and permanent contraction of the muscle (7). Consequently, DMB treatment induces a "rigid" phenotype of the lower limb, effectively imposing a static (zero frequency) load on the calcaneal tendon. Here, mechanical testing of the calcaneal tendons revealed that paralysis reduced modulus by 2-fold relative to controls (FIG. 1A). To induce hypermotility, embryos were treated with 4-AP, a potassium channel blocker that prolongs depolarization at the neuromuscular junctions to stimulate continuous firing of muscle contraction (8). 4-AP treatment increased embryo movement frequency by 200% within 1 min of injection, which lasted 48 h (data not shown). Mechanical testing of calcaneal tendons showed that 4-AP treatment increased modulus by 2-fold relative to controls (FIG. 1A). Collectively, these results suggest embryo movement is critically required for the normal development of tendon mechanical properties, and that it is possible to enhance tendon mechanical properties by increasing movement frequency.

(b) LOX Levels Increase During Development but LOXL1-4 Levels do not

Interestingly, collagen content and apparent collagen organization did not change with either treatment relative to controls (FIGS. 1B and 1C). On the basis of these findings, it was asked whether LOX is involved in the mechanically induced changes in modulus. LOX and LOXL family members have been shown to exhibit similar catalytic functions (16). To examine which LOX family members may be involved in the development of embryonic tendon mechanical properties, mRNA levels of LOX and LOXL family members were examined (FIG. 2). It was found that LOXL1 to 4 levels either remained constant or decreased during development. In contrast, LOX levels increased beginning at HH39, peaked at HH42, and then plateaued through HH45. LOX was the only family member that increased during development. Because elastic modulus also increases during development, LOX was further studied.

ProLOX and LOX activity levels each exhibited distinct stage-specific trends, with dramatic increases at the latest stages. Interestingly, movement frequency increases in a stage-specific manner, and also increases dramatically at the latest stages (11). Chick embryo bilateral limb movement frequency peaks at HH43 (11). Coincidentally, LOX activity levels increased significantly from HH42 to HH43 (FIG. 3B). Notably, LOX activity levels (FIG. 3B) also correlated most highly with previously reported developing embryonic tendon moduli (10), ($r^2$=0.97; $p<0.05$) (Table 2). Based on these data, it was hypothesized that movement regulates mechanical property development of calcaneal tendon, and that these events involve LOX.

TABLE 2

Pearson's correlation between previously reported elastic moduli (10) and LOX levels (mRNA, proLOX, LOX activity) for HH38 to HH43 calcaneal tendons.

|  | Residual value ($r^2$) | p-value |
|---|---|---|
| LOX mRNA vs. modulus | 0.56 | 0.25 |
| proLOX vs. modulus | 0.93 | 0.034 |
| LOX activity vs. modulus | 0.97 | 0.016 |

(c) Paralysis Downregulates LOX Activity

DMB treatment downregulated LOX activity levels of calcaneal tendons by 2-fold compared to saline controls ($p<0.05$) (FIG. 4A), paralleling the 2-fold decrease in modulus (FIG. 1A). To test whether this decrease in LOX activity levels was due specifically to rigid paralysis induced by DMB, flaccid paralysis was induced via PB treatment. PB-induced flaccid paralysis also led to 2-fold reductions in LOX activity levels relative to controls ($p<0.05$) (FIG. 4A). Taken together, the two different methods to induce paralysis led to similar reductions in LOX activity levels. To confirm these results were due to paralysis and not the chemical treatment itself, isolated legs were cultured ex ovo with DMB- or saline-supplemented growth medium for 48 h. No changes in tendon LOX activity levels were detected (FIG. 4B), suggesting reductions in LOX activity levels after paralysis were not due to biochemical effects of DMB. These results strongly implicate LOX as an important player in how normal embryo movement regulates the development of tendon mechanical properties.

Collagen content and organization of both DMB- and 4-AP-treated tendons appeared normal despite decreases in modulus and LOX activity levels (FIGS. 1B and 1C). This was consistent with study that showed inhibition of LOX activity decreases embryonic tendon moduli via reductions in LOX-mediated collagen crosslink density, and that this occurs without affecting collagen content or organization (10, 12). Perhaps DMB-induced paralysis led to decreases in LOX activity, which in turn reduced collagen crosslinking, which then led to the decrease in modulus. Future studies could use mass spectrometry to measure changes in LOX-mediated crosslink density (12).

(d) Hypermotility-Induced Enhancement of Tendon Modulus May Involve LOX

LOX activity levels did not differ between 4-AP and saline treatments (FIG. 4A). A previous study with osteoblasts detected increases in LOX activity at 18 h after treatment (17). Based on this, it is possible that the 48 h timepoint tested was too late, and missed a window of time during which LOX activity levels were higher. To test the potential involvement of LOX with an alternative approach, embryos were treated with 4-AP+BAPN to induce hyperactivity and inhibit LOX activity simultaneously. Strikingly, 4-AP+BAPN treatment led to reductions in calcaneal tendon modulus compared to 4-AP treatment (hypermotility) alone, and was statistically similar to controls (FIG. 5). BAPN treatment reduced modulus. Notably, despite differences in tendon elastic modulus, apparent collagen organization appeared normal after 4-AP, 4-AP+BAPN, and BAPN treatments.

TABLE 3

Average stage of chick embryos treated with saline, DMB, 4-AP, 4-AP + BAPN, and BAPN at HH43 for 48 h (N ≥ 6). Expected stage after 48 h treatment is HH45. Statistical analysis was performed to compare average stage of each group with saline control.

|  | Saline | DMB | 4-AP | 4-AP+BAPN | BAPN |
|---|---|---|---|---|---|
| Stage (HH) of embryos at harvest (mean ± standard deviation (std)) | 45 ± 0.6 | 45 ± 0.4 | 45 ± 0.4 | 44 ± 0.5 | 45 ± 0.5 |
| p value (compared to saline control) | $p > 0.05$ | $p > 0.05$ | $p > 0.05$ | *$p < 0.05$ | $p > 0.05$ |

Example 7 Treatment with Exogenous LOX Increased Elastic Modulus

In this example, assays were carried out to examine effects of exogenous LOX on elastic modulus of HH40 explant calcaneal tendons.

Briefly, HH40 explant calcaneal tendons were either cultured in a growth medium supplemented with recombinant LOX (rLOX) (ORIGENE) or a saline (vehicle control) medium. The growth medium contained 10% fetal bovine serum and 1% antibiotic-antimycotic in high glucose Dulbecco's Modified Eagle Medium (DMEM). Treatment of rLOX was performed at 0 h and 24 h. The growth medium were changed at 24 h. The explant tendons were then tested using tensile mechanical testing at 60 h. Two concentrations of rLOX were used: 0.15 μg/uL and 1.5 μg/uL. The results are shown in FIG. 7.

Figure 7:
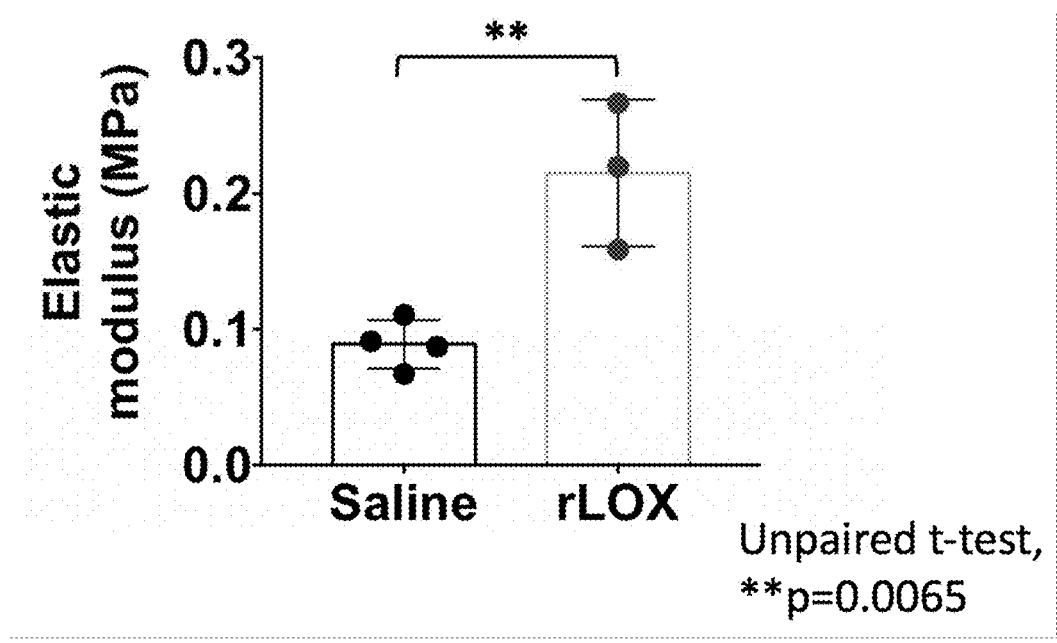
FIG. 7 is a diagram showing that treatment with an exogenous recombinant LOX (rLOX) increased elastic modulus of HH40 explant calcaneal tendons relative to saline controls. Data points for two rLOX treatments were combined together to have N=3 for the rLOX-treated group.

As shown in FIG. 7, the rLOX-treated explant tendons possessed significantly higher elastic modulus compared to saline-treated samples after 60 hours in culture. These results strongly indicate LOX as an important player in enhancing mechanical properties of tendon.

Example 8 Effect of Rigid and Flaccid Paralysis on Calcaneal Tendon HP Crosslink Density Normalized to Collagen Content In this example, assays were carried out to examine effects of DMB-induced rigid paralysis and PB-induced flaccid paralysis on density of collagen crosslinker hydroxylysyl pyridinoline.

Figure 8:
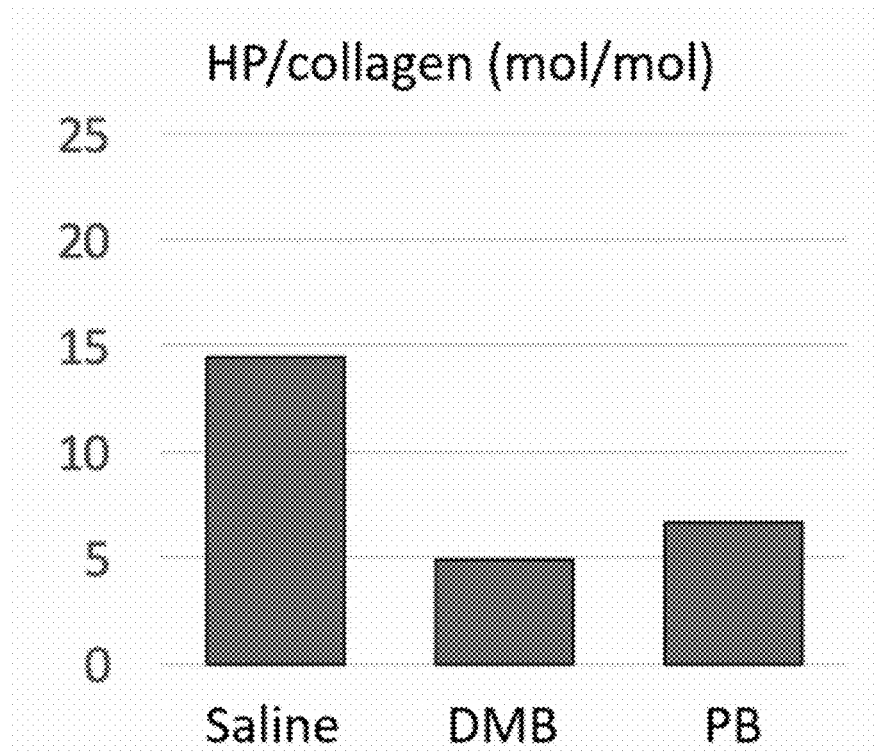
FIG. 8 is a diagram showing effects of paralysis (no movement), induced by either DMB or PB treatment, on density of collagen crosslinker hydroxylysyl pyridinoline (HP).

Briefly, HH43 chick embryos were either treated with saline (vehicle control), decamethonium bromide (DMB, THERMO FISHER), or pancuronium bromide (PB, THERMO FISHER). Treatments of DMB and PB were performed at 0 h and 24 h by injection through the air-pocket of each egg. After the 48 h of treatments, each embryo was sacrificed by decapitation, was staged, and the calcaneal tendons were dissected for collagen cross-link density analysis. For each biological sample (N=1), 5 tendons were pooled together (5 left calcaneal tendons from 5 chick embryos). In this experiment, collagen crosslink density analysis was performed for biological samples. The results are shown in FIG. 8. As shown in FIG. 8, both DMB- and PB-treated tendons possessed lower hydroxylysyl pyridinoline (HP)/collagen ratio compared to the saline-treated tendons after 48 h of paralysis. The results indicate that paralysis induced by DMB treatment or PB treatment each decreased collagen cross-linking.

REFERENCES

1. Nowlan N C, Chandaria V, Sharpe J. Immobilized chicks as a model system for early-onset developmental dysplasia of the hip. J Orthop Res. 2014; 32(6):777-85.
2. Verbruggen S W, Kainz B, Shelmerdine S C, Hajnal J V, Rutherford M A, Arthurs O J, et al. Stresses and strains on the human fetal skeleton during development. Journal of The Royal Society Interface. 2018; 15(138):20170593.
3. Mikic B, Wong M, Chiquet M, Hunziker E B. Mechanical modulation of tenascin-C and collagen-XII expression during avian synovial joint formation. J Orthop Res. 2000; 18(3):406-15.
4. Hall B K, Herring S W. Paralysis and growth of the musculoskeletal system in the embryonic chick. J Morphol. 1990; 206(1):45-56.
5. Pollard A S, Boyd S, McGonnell I M, Pitsillides A A. The role of embryo movement in the development of the furcula. Journal of anatomy. 2017; 230(3):435-43.
6. Havis E, Bonnin M A, Esteves de Lima J, Charvet B, Milet C, Duprez D. TGFbeta and FGF promote tendon progenitor fate and act downstream of muscle contraction to regulate tendon differentiation during chick limb development. Development. 2016; 143(20):3839-51.
7. Mitrovic D. Development of the articular cavity in paralyzed chick embryos and in chick embryo limb buds cultured on chorioallantoic membranes. Acta anatomica. 1982; 113(4):313-24.
8. Osborne A C, Lamb K J, Lewthwaite J C, Dowthwaite G P, Pitsillides A A. Short-term rigid and flaccid paralyses diminish growth of embryonic chick limbs and abrogate joint cavity formation but differentially preserve pre-cavitated joints. Journal of musculoskeletal & neuronal interactions. 2002; 2(5):448-56.
9. Heywood J L, McEntee G M, Stickland N C. In ovo neuromuscular stimulation alters the skeletal muscle phenotype of the chick. J Muscle Res Cell Motil. 2005; 26(1):49-56.
10. Marturano J E, Arena J D, Schiller Z A, Georgakoudi I, Kuo C K. Characterization of mechanical and biochemical properties of developing embryonic tendon. Proc Natd Acad Sci USA. 2013; 110(16):6370-5.
11. Wu K C, Streicher J, Lee M L, Hall B K, Muller G B. Role of motility in embryonic development I: Embryo movements and amnion contractions in the chick and the influence of illumination. J Exp Zool. 2001; 291(2):186-94.
12. Marturano J E, Xylas J F, Sridharan G V, Georgakoudi I, Kuo C K. Lysyl oxidase-mediated collagen crosslinks may be assessed as markers of functional properties of tendon tissue formation. Acta Biomater. 2014; 10(3):1370-9.
13. Fujimoto D. Isolation and characterization of a fluorescent material in bovine achilles tendon collagen. Biochemical and biophysical research communications. 1977; 76(4):1124-9.
14. Pitsillides A A. Early effects of embryonic movement: 'a shot out of the dark'. Journal of anatomy. 2006; 208(4):417-31.
15. Hamburger V, Hamilton HL. A series of normal stages in the development of the chick embryo. J Morphol. 1951; 88(1):49-92.
16. Kim Y, Boyd C D, Csiszar K. A new gene with sequence and structural similarity to the gene encoding human lysyl oxidase. The Journal of biological chemistry. 1995; 270 (13):7176-82.
17. Feres-Filho E J, Choi Y J, Han X, Takala T E, Trackman P C. Pre- and post-translational regulation of lysyl oxidase by transforming growth factor-beta 1 in osteoblastic MC3T3-E1 cells. The Journal of biological chemistry. 1995; 270(51):30797-803.
18. Heinemeier K M, Olesen J L, Haddad F, Langberg H, Kjaer M, Baldwin K M, et al. Expression of collagen and related growth factors in rat tendon and skeletal muscle in response to specific contraction types. J Physiol. 2007; 582(Pt 3):1303-16.
19. McNemy E M B, Gardinier J D, Kohn D H. Exercise increases pyridinoline cross-linking and counters the mechanical effects of concurrent lathyrogenic treatment. Bone. 2015; 81:327-37.
20. Birk D E, Fitch J M, Babiarz J P, Doane K J, Linsenmayer T F. Collagen fibrillogenesis in vitro: interaction of types I and V collagen regulates fibril diameter. Journal of cell science. 1990; 95 (Pt 4):649-57.
21. Birk D E, Zycband E I, Woodruff S, Winkelmann D A, Trelstad R L. Collagen fibrillogenesis in situ: fibril segments become long fibrils as the developing tendon matures. Developmental dynamics: an official publication of the American Association of Anatomists. 1997; 208 (3):291-8.
22. Brent A E, Schweitzer R, Tabin C J. A somitic compartment of tendon progenitors. Cell. 2003; 113(2):235-48.
23. Schweitzer R, Chyung J H, Murtaugh L C, Brent A E, Rosen V, Olson E N, et al. Analysis of the tendon cell fate using Scleraxis, a specific marker for tendons and ligaments. Development. 2001; 128(19):3855-66.
24. Canty E G, Lu Y, Meadows R S, Shaw M K, Holmes D F, Kadler K E. Coalignment of plasma membrane channels and protrusions (fibripositors) specifies the parallelism of tendon. J Cell Biol. 2004; 165(4):553-63.
25. Marturano J E, Schiele N R, Schiller Z A, Galassi T V, Stoppato M, Kuo C K. Embryonically inspired scaffolds regulate tenogenically differentiating cells. J Biomech. 2016; 49(14):3281-8.
26. Schiele N R, von Flotow F, Tochka Z L, Hockaday L A, Marturano J E, Thibodeau J J, et al. Actin cytoskeleton contributes to the elastic modulus of embryonic tendon during early development. J Orthop Res. 2015; 33(6):874-81.
27. Kuo C K, Petersen B C, Tuan R S. Spatiotemporal protein distribution of TGF-betas, their receptors, and extracellular matrix molecules during embryonic tendon development. Developmental dynamics: an official publication of the American Association of Anatomists. 2008; 237(5):1477-89.
28. Brown J P, Finley V G, Kuo C K. Embryonic mechanical and soluble cues regulate tendon progenitor cell gene expression as a function of developmental stage and anatomical origin. J Biomech. 2014; 47(1):214-22.

29. Brown J P, Galassi T V, Stoppato M, Schiele N R, Kuo C K. Comparative analysis of mesenchymal stem cell and embryonic tendon progenitor cell response to embryonic tendon biochemical and mechanical factors. Stem Cell Res Ther. 2015; 6:89.
30. Kuo C K, Tuan R S. Mechanoactive tenogenic differentiation of human mesenchymal stem cells. Tissue Eng Part A. 2008; 14(10):1615-27.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A pharmaceutical composition comprising
   (i) lysyl oxidase (LOX) or LOX like (LOXL) protein (LOX/LOXL) enhancer selected from the group consisting of a LOX polypeptide, a LOXL protein, a pre-proLOX polypeptide, a proLOX polypeptide, a nucleic acid encoding one or more of the polypeptides, an engineered cell expressing or having said nucleic acid, and a viral particle having the nucleic acid,
   (ii) an agent selected from the group consisting of BMP-1, Fibronectin, Tolloid, Vitamin B6, Ascorbic acid, and Procollagen c proteinase, and
   (iii) a pharmaceutically acceptable carrier or excipient.

2. The pharmaceutical composition of claim 1, wherein the pharmaceutical composition is formulated in an ointment, a salve, a gel, a cream, a scaffold, or a microparticle.

3. A kit comprising
   a LOX/LOXL enhancer selected from the group consisting of a LOX polypeptide, a LOXL protein, a pre-proLOX polypeptide, a proLOX polypeptide, a nucleic acid encoding one or more of the polypeptides, an engineered cell expressing or having said nucleic acid, and a viral particle having the nucleic acid,
   an agent selected from the group consisting of BMP-1, Fibronectin, Tolloid, Vitamin B6, Ascorbic acid, and Procollagen c proteinase, and
   a packaging material.

4. A method for (i) improving a mechanical property of a tissue or a component thereof in a subject or (ii) regenerating an injured tissue or diseased tissue or developing embryonic/fetal tissue or a component thereof in a subject or (iii) enhancing mechanical properties of a healthy tissue in a subject, comprising (a) applying a mechanical stimulation to the tissue or cells therein and (b) administering to the subject the pharmaceutical composition of claim 1.

5. The method of claim 4, wherein said mechanical stimulation comprises one or more of a dynamic stimulation, a cyclic stimulation, a static stimulation, a deformation, a tensile stimulation, a compressive stimulation, a torsion stimulation, a shear stimulation, substrate stiffness, a mechanical loading, a static loading, a dynamic loading, a cyclic loading, a compression, shear, torsion, and deformation.

6. The method of claim 4, wherein the tissue is a natural tissue, an engineered tissue, an embryonic tissue, a postnatal tissue, a tissue in vitro, or a tissue in vivo.

7. The method of claim 6, wherein the tissue is a collagenous or collagen-containing tissue.

8. The method of claim 4, wherein the mechanical property is selected from the group consisting of elastic modulus, tensile strength, torsional strength, elongation to break, hardness, compressive strength, burst strength, toughness, impact strength, torsion, failure load, and stiffness.

9. The method of claim 4, further comprising administering a population of cells to the tissue.

10. The method of claim 9, wherein the cells are (i) collagen-producing or elastin-producing cells or progenitor cells thereof or (ii) engineered to release a specific factor that directly or indirectly promotes LOX/LOXL or pro-LOX/pro-LOXL gene expression, LOX/LOXL or pro-LOX/pro-LOXL protein expression, or LOX/LOXL enzyme activity.

11. A method for (i) improving a mechanical property of a tissue or a component thereof in a subject or (ii) regenerating an injured tissue, a diseased or developing embryonic/fetal tissue, or a component thereof in a subject, comprising administering to the subject the pharmaceutical composition of claim 1.

12. The method of claim 11, wherein the tissue is a natural tissue, an engineered tissue, a tissue in vitro, or a tissue in vivo.

13. The method of claim 12, wherein the tissue is a collagenous or collagen-containing tissue or an elastin-containing tissue.

14. The method of claim 11, wherein the mechanical property is selected from the group consisting of elastic modulus, tensile strength, torsional strength, elongation to break, hardness, compressive strength, burst strength, toughness, impact strength, torsion, failure load, and stiffness.

15. The method of claim 11, further comprising administering a population of cells to the tissue.

16. The method of claim 15, wherein the cells are (i) collagen-producing cells, elastin-producing cells or progenitor cells thereof or (ii) engineered to release a specific factor that directly or indirectly promotes LOX/LOXL gene expression, LOX/LOXL protein expression, or LOX/LOXL enzyme activity.

17. The method of claim 4, wherein this tissue is a tendon tissue or a ligament tissue.

18. The method of claim 11, wherein this tissue is a tendon tissue or a ligament tissue.

* * * * *